(12) United States Patent
Baird et al.

(10) Patent No.: US 6,479,654 B1
(45) Date of Patent: Nov. 12, 2002

(54) FORMS OF THE ANGIOGENIC FACTOR VASCULAR ENDOTHELIAL CELL GROWTH FACTOR: VEGF

(75) Inventors: Andrew Baird, San Diego, CA (US); Grai Andreason, La Jolla, CA (US)

(73) Assignee: Collateral Therapeutics, San Diego, CA (US)

( * ) Notice: Subject to any disclaimer, the term of this patent is extended or adjusted under 35 U.S.C. 154(b) by 0 days.

(21) Appl. No.: 09/244,583

(22) Filed: Feb. 4, 1999

Related U.S. Application Data

(60) Provisional application No. 60/073,979, filed on Feb. 6, 1998.

(51) Int. Cl.$^7$ .................. C07H 21/04; C07H 21/02; C12N 15/00; C12N 15/09; C12N 15/63
(52) U.S. Cl. ................. 536/23.5; 536/23.1; 435/320.1
(58) Field of Search ................. 424/93.1, 93.2; 435/69.1, 320.1, 172.3; 514/44; 536/23.1, 23.5

(56) References Cited

U.S. PATENT DOCUMENTS

| | | | |
|---|---|---|---|
| 5,194,596 A | | 3/1993 | Tischer et al. |
| 5,240,848 A | | 8/1993 | Keck et al. |
| 5,328,470 A | | 7/1994 | Nabel et al. |
| 5,652,225 A | | 7/1997 | Isner |
| 5,661,133 A | | 8/1997 | Leiden et al. |
| 5,698,531 A | | 12/1997 | Nabel et al. |
| 5,707,969 A | | 1/1998 | Nabel et al. |
| 5,792,453 A | | 8/1998 | Hammond et al. |
| 5,869,037 A | * | 2/1999 | Crystal et al. .............. 424/93.2 |
| 6,013,780 A | * | 1/2000 | Neufeld et al. ............. 536/23.1 |
| 6,100,242 A | | 8/2000 | Hammond et al. |

FOREIGN PATENT DOCUMENTS

| | | |
|---|---|---|
| AU | 27902/92 | 4/1993 |
| WO | WO 90/13649 | 11/1990 |
| WO | WO 91/02058 | 2/1991 |
| WO | WO 94/11506 | 5/1994 |
| WO | WO 95/00655 | 1/1995 |
| WO | WO 96/26736 | 9/1996 |
| WO | WO 96/26742 | 9/1996 |
| WO | WO 96/27007 | 9/1996 |
| WO | WO 96/39421 | 12/1996 |
| WO | WO 97/05250 | 2/1997 |
| WO | WO 97/08313 | 3/1997 |
| WO | WO 98/10071 | 3/1998 |

OTHER PUBLICATIONS

Adamis et al., "Increased Vascular Endothelial Growth Factor Levels in the Vitreous of Eyes With Proliferative Diabetic Retinopathy," *Am. J. Ophthalmol.* 118:445–450 (1994).

Aiello et al., "Vascular Endothelial Growth Factor in Ocular Fluid of Patients with Diabetic Retinopathy and Other Retinal Disorders," *New England J. Med.* 331:1480–1487 (1994).

Anthony et al., "Short Report: Identification of a Specific Pattern of Vascular Endothelial Growth Factor mRNA Expression in Human Placenta and Cultured Placental Fibroblasts," *Placenta* 15:557–561 (1994).

Asahara et al., "Local Delivery of Vascular Endothelial Growth Factor Accelerates Reendothelization and Attenuates Intimal Hyperplasia in Balloon–Injured Rat Carotid Artery," *Circulation* 91:2793–2801 (1995).

Asahara et al., "Synergistic Effect of Vascular Endothelial Growth Factor and Basic Fibroblast Growth Factor on Angiogenesis In vivo," *Circulation* 92[suppl II]:II–365 to II–371 (1995).

Bacic et al., "Differential Expression of Vascular Endothelial Growth Factor (Vascular Permeability Factor) Forms in Rat Tissues," *National Institutes of Health, Bethesda,MD 20892, USA* 11–15 (1994).

Banai et al.,"Upregulation of vascular endothelial growth factor expression induced by myocardial ischaemia: implications for coronary angiogenesis," *Cardiovascular Research* 28:1176–1179 (1994).

Bauters et al., "Physiological assessment of augmented vascularity induced by VEGF in ischemic rabbit hindlimb," *Am. J. Physiol.* 267:H1263–H1271 (1994).

Bauters et al., "Recovery of Disturbed Endothelium–Dependent Flow in the Collateral–Perfused Rabbit Ischemic Hindlimb After Administration of Vascular Endothelial Growth Factor," *Circulation* 91:2802–2809 (1995).

Bauters et al., "Site–specific therapeutic angiogenisis after systemic administration of vascular endothial growth factor," *J. Vasc. Surg.* 21:314–325 (1995).

Brogi, et al., "Indirect Angiogenic Cytokines Upregulate VEGF and bFGF Gene Expression in Vascular Smooth Muscle Cells," Whereas Hypoxia Upregulates VEGF Expression only, Circulation 90:649–652 (1994).

(List continued on next page.)

Primary Examiner—Scott D. Priebe
Assistant Examiner—Peter Paras, Jr.
(74) *Attorney, Agent, or Firm*—Gray Cary Ware & Freidenrich LLP

(57) ABSTRACT

Novel forms of vascular endothelial growth factor genes and the novel proteins encoded by these genes are disclosed. More particularly, novel forms of human VEGF-A which contain exon 6b and do not contain exon 6a are disclosed. Other novel forms of human VEGF-A contain exon 6b in addition to exon 6a. These novel forms of VEGF-A include VEGF-$A_{138}$, VEGF-$A_{162}$, and VEGF-$A_{182}$. Such novel VEGF proteins may be used in treatment of the cardiovascular system and its diseases through effects on anatomy, conduit function, and permeability, and more particularly in the treatment of cardiovascular disease by stimulating vascular cell proliferation using a growth factor, thereby stimulating endothelial cell growth and vascular permeability. The invention also relates to nucleic acids encoding such novel VEGF proteins, cells, tissues and animals containing such nucleic acids; methods of treatment using such nucleic acids; and methods relating to all of the foregoing.

6 Claims, 6 Drawing Sheets

OTHER PUBLICATIONS

Brown et al., "Expression of Vascular Permeability Factor (Vascular Endothelial Growth Factor) by Epidermal Keratinocytes during Wound Healing," *J. Exp. Med.* 176:1375–1379 (1992).

Cao, et al., "Heterodimers of Placenta Growth Factor/Vascular Endothelial Growth Factor," J. Biol. Chem 271(6):3154–3162 (1996).

Carmeliet et al., "Abnormal blood vessel development and lethality in embryos lacking a single VEFG allele," *Nature* 380:435–438 (1996).

Charnock–Jones et al., "Identification and Localization of Alternately Spliced mRNAs for Vascular Endothelial Growth Factor in Human Uterus and Estrogen Regulation in Endometrial Carcinoma Cell Lines," *Biology of Reproduction* 48:1120–1128 (1993).

Cheung et al., "Vascular Endothelial Growth Factor Gene Expression in Ovine Placenta and Fetal Membranes," *AM J Obstet Bynecol* 173:751–759 (1995).

Cohen, et al., "VEGF 121, a Vascular Endothelial Growth Factor (VEGF) Isoform Lacking Heparin Binding Ability, Requires Cell–surface Heparin Sulfate for Efficient Binding to the VEGF Receptors of Human Melanoma Cells," J. Biol. Chem. 270(19):11322–11326 (1995).

Cohen, et al., *Growth Factors* 7:131–138 (1992).

Connoly, et al., "Human Vascular Permeability Factor: Isolation from U937 Cells," J. Biol. Chem. 264:20017–20024 (1989).

Cullinan–Bove and Koos, "Vascular Endothelial Growth Factor/Vascular Permeability Factor Expression in the Rat Uterus: Rapid Stimulation by Estrogen Correlates with Estrogen–Induced Increases in Uterine Capillary Permeability and Growth," *Endocrinology* 133(2):829–837 (1993).

De Vries et al., "The fms–Like Tyrosine Kinase, a Receptor for Vascular Endothelial Growth Factor," *Science* 255:989–991 (1992).

Detmar et al., "Overexpression of Vascular Permeability Factor/Vascular Endothelial Growth Factor and its Receptors in Psoriasis," *J. Exp. Med.* 180:1141–1146 (1994).

DiSalvo, et al., "Purification and Characterization of a Naturally Occurring Vascular Endothelial Growth Factor—Placenta Growth Factor Heterodimer," J. Biol. Chem. 270:7717–7723 (1995).

Dvorak et al., "Vascular Permeability Factor/Vascular Endothelial Growth Factor, Microvascular Hyperpermeability, and Angiogeneiss," *Am. J. Pathol.* 146:1029–1039 (1995).

Fava et al., "Vascular Permeability Factor/Endothelial Growth Factor (VPF/VEGF): Accumulation and Expression in Human Synovial Fluids and Rheumatoid Synovial Tissue," *J. Exp. Med.* 180:341–346 (1994).

Favard, et al., *Biol. Cell,* 73: 1–6 (1991). (Chemotactic nature of VEGF–A).

Ferrara et al., "Molecular and Biological Properties of the Vascular Endothelial Growth Factor Family of Proteins," *Endocrine Reviews* 13:18–32 (1992).

Fiebich, et al., "Synthesis and assembly of functionally active human vascular endothelial growth factor homodimers in insect cell," Eur.J. Biochem. 211:19–26 (1993).

Flotte, et al. *Gene Therapy* 2:357–362 (1995).

Frank et al., "Regulation of Vascular Endothelial Growth Factor Expression in Cultured Keratinocytes," *J. Biol. Chem.* 270:12607–12613 (1995).

French, et al., "Gene Transfer and cardiovascular disorders," Herz, vol. 18(4):222–229 (1993).

Giordano, et al., "Reduced Myocardial Ischemia After Recombinant Adenovirus Mediated In–Vivo Fibroblast Growth Factor–5 Gene Transfer," J. Investigative Med., Supplement 2, vol. 43:287A (1995).

Giordano, et al., "Adenoviral Based In–Vivo Gene Transfer in the Pig," Clin. Res., vol. 42:123A (1994).

Giordano, et al., "Intracoronary gene transfer of fibroblast growth factor–5 increases blood flow and contractile function in an ischemic region of the heart," Nature Medicine, vol. 2(5):534–539 (1996).

Gitay–Goren et al., "Selective Binding of $VEGF_{121}$ to One of the Three Vascular Endothelial Growth Factor Receptors of Vascular Endothelial Cells," *J. Biol. Chem.* 271:5519–5523 (1996).

Gospodarowicz et al., "Isolation and characterization of a vascular endothelial cell mitogen produced by pituitary–derived folliculo stellate cells," *Proc. Natl. Acad. Sci. USA* 86:7311–7315 (1989).

Grimmond, et al., "Cloning and Characterization of a Novel Human Gene Related to Vascular Endothelial Growth Factor," Genome Research 6:122–129 (1996).

Hashimoto et al., "Rapid induction of vascular endothelial growth factor expression by transient ischemia in rat heart," *Am. J. Physiol.* 267:H1948–H1954 (1994).

Houck et al., "Dual Regulation of Vascular Endothelial Growth Factor Bioavailability by Genetic Proteolytic Mechanisms," *The Journal of Biological Chemistry* 267(36):26031–26037 (1992).

Houck et al., "The Vascular Endothelial Growth Factor Family: Identification of a Fourth Molecular Species and Characterization of Alternative Splicing of RNA" *Molecular Endocrinology* 5:1806–1814 (1991).

Jackson et al., "Localization of Two Angiogenic Growth Factors (PDECGF and VEGF) in Human Placentae Throughout Gestation," *Placenta* 15:341–353 (1994).

Jonca, et al., "Cell Release of Bioactive Fibroblast Growth Factor 2 by Exon 6–encoded Sequence of Vascular Endothelial Growth Factor," Journal of Biological Chemistry, vol. 272, No. 39, Sep. 26, 1997 (1997–09–26), pp. 24203–24209.

Kamat et al., "Expression of Vascular Permeability Factor/Vascular Endothelial Growth Factor by Human Granulosa and Theca Lutein Cells," *American Journal of Pathology* 146:157–165 (1995).

Keyt et al., "Identification of Vascular Endothelial Growth Factor Determinants for Binding KDR and FLT–1 Receptors," *The American Society for Biochemistry and Molecular Biology, Inc.* 5638–5646 (1996).

Keyt et al., "The Carboxyl–terminal Domain (111–165) of Vascular Endothelial Growth Factor is Critical for Its Mitogenic Potency," *J. Biol. Chem.* 271:7788–7795 (1996).

Klagsbrun, et al., Vascular Endothelial Growth Factor and its Receptors, *Cytokine & Growth Factor Reviews,* vol. 7, No. 3, pp. 259–270, 1996.

Ku et al., "Vascular endothelial growth factor induces EDRF–dependent relaxation in coronary arteries," *Am. J. Physiol.* 265:H586–H592 (1993).

Lazarous, et al., "Comparative Effects of Basic Fibroblast Growth factor and Vascular Endothelial Growth Factor on Coronary Collateral Development and the Arterial Response to Injury," Circulation, vol. 94(5), 1074, (1996).

Leung et al., "Vascular Endothelial Growth Factor is a Secreted Angiogenic Mitogen," Science 246:1306–1309 (1989).

Levy et al., "Post–transcriptional Regulation of Vascular Endothelial Growth Factor by Hypoxia," J. Biol. Chem. 271:2746–2753 (1996).

Mandriota et al., "Vascular Endothelial Growth Factor Increases Urokinase Receptor Exprsesion in Vascular Endothelial Cells," J. Biol. Chem. 270:9709–9916 (1995).

Miller et al., "Vascular Endothelial Growth Factor/Vascular Permeability Factor is Temporarily and Spatially Correlated with Ocular Angiogenesis in a Primate Model," Am. J. Pathol. 145:574–584 (1994).

Miller, et al., "Targeted vectors for gene therapy," FASEB J. (1995) 9:190–199.

Mohanraj, et al., "A Novel Method to Purify Recombinant Vascular Endothelial Growth Factor (VEGF 121) Expression in Yeast," Biochem, Biophys, Res. Commun. 215:750–756 (1995).

Muhlhaser, et al., "VEGF 165 Expressed by a Replication-–Deficient Recombinant Adenovirus Vector Induces Angiogenesis In Vivo," Circulation Research, vol. 77(6):1077–1086 (1995).

Nabel, "Gene Therapy for Cardiovascular Disease," Circulation 91(2):541–549 (1995).

Neufeld et al., "Similarities and Difference Between the Vascular Endothelial Growth Factor (VEGF Splice Variants," Cancer and Metastasis Reviews 15:153–158 (1996).

Nicosia et al., "Vascular Endothelial Growth Factor, Platelet–Derived Growth Factor, and Insulin–Like Growth Factor–1 Promote Rat Aortic Angiogenesis In Vitro," Am. J. Pathol. 145:1023–1029 (1994).

Park, et al., "The Vascular Endothelial Growth Factor (VEGF) Isoforms: Differential Deposition into the Subepithelial Extracellular Matrix and Bioactivity of Extracellular Matrix–bound VEGF," Molecular and Cellular Biology 4:1317–1326 (1993).

Pepper et al., "Vascular Endothelial Growth Factor (VEGF) Induces Plasminogen Activators and Plasminogen Activator Inhibitor–1 in Microvascular Endothelial Cells," Biochemical and Biophysical Research Communications 181:902–906 (1991).

Pepper, et al., "Potent synergism between vascular endothelial growth factor and basic fibroblast growth factor and basic fibroblast growth factor in the induction of angiogenesis in vitro," Biochemical and Biophysical Research Communications, vol. 189, No. 2, Dec. 15, 1992, pp. 824–831, XP002078851.

Peters et al., "Vascular endothelial growth factor receptor expression during embryogenesis and tissue repair suggests a role in endothelial differentiation and blood vessel growth," Proc. Natl. Acad. Sci. USA 90:8915–8919 (1993).

Plouet, et al., "Isolation and characterization of newly identified endothelial cell mitogen produced by AtT–20 Cells," EMBO I, 8:3801–3806 (1989).

Plunkett et al., "An In Vivo Quantitative Angiogenesis Model Using Tumor Cells Entrapped in Alginate," Laboratory Investigation 62(4):510–517 (1990).

Poltorack, et al., "VEGF 145, a secreted V.E.G.F. isoform that binds to extra–cellular matrix," Journ. of Biol. Chem. 272(11):7151–7158 (1997).

Potgens et al., "The Role of Vascular Permeability Factor and Basic Fibroblast Growth Factor in Tumor Angiogenesis," Biol. Chem. Hoppe–Seyler 376:57–70 (1995).

Potgens, et al., "Covalent Dimerization of Vascular Permeability Factor/Vascular Endothelial Growth Factor is Essential for its Biological Activity," J. Biol. Chem. 269:32879–32885 (1994).

Pu et al., "Enhanced Revascularization of the Ischemic Limb by Angiogenic Therapy," Circulation 88:208–215 (1993).

Risau and Flamme, "Vasculogenesis," Annu. Rev. Cell. Dev. Biol. 11:73–91 (1995).

Rowland, et al., "Potential Gene Therapy Strategies in the Treatment of Cardiovascular Disease," Am. Thorc. Surg., 60(3):721–718 (1995).

Shweiki, et al., "Patterns of Expression of Vasc. Endo. G.F. (VEGF) and VEGF Receptors in Mice Suggest a Role in Hormonally Regulated Angiogenesis," J. Clin. Invest., 91(5):2235–43 (1993).

Shweiki, et al., "Vascular endothelial Growth Factor Induced by Hypoxia May Mediate Hypoxia–Initiated Angiogenesis," Nature, 359(6398):843–45 (1992).

Takeshita et al., "Intramuscular Administration of Vascular Endothelial Growth Factor Induces Dose–Dependent Collateral Artery Augmentation in a Rabbit Model of Chronic Limb Ischemia," Circulation 90 [part 2]: II–228 to II–234 (1994).

Takeshita et al., "Therapeutic Angiogensis: A Single Intraarterial Bolus of Vascular Endoethelial Growth Factor Augments Revascularization in a Rabbit Ischemic Hind Limb Model," J. Clin. Invest. 943:662–670 (1994).

Terman et al., "Identification of the KDR Tyrosine Kinase as a Receptor for Vascular Endothelial Cell Growth Factor," Biochem. Biophys. Res. Commun. 187:1579–1586 (1992).

Terman et al., "VEGF Receptor Subtypes KDR and FLT1 Show Different Sensitivities to Heparin and Placenta Growth Factor," Growth Factors 11:187–195 (1994).

Thomas, "Vascular Endothelial Growth Factor, a Potent and Selective Angiogenic Agent," J. Biol. Chem. 271:603–606 (1996).

Tischer et al., "The Human Gene for Vascular Endothelial Growth Factor," J. Biol. Chem. 266:11947–11954 (1991).

Tischer, et al., "Vascular Endothelial Growth Factor: A New Member of the Platelet–derived Growth Factor Gene Family," Biochemical and Biophysical Research Communications 165:1198–1206 (1989).

Unemori et al., "Vascular Endothelial Growth Factor Induces Interstitial Collagenase Expression in Human Endothelial Cells," J. Cell. Physiol. 153:557–562 (1992).

Wilting, et al., "VEGF 121 Induces Proliferation of Vascular Endothelial Cells and Expression of flk–1 without Affecting Lymphatic Vessels of the Chorioallantoic Membrane," Developmental Biology 176:76–85 (1996).

Alberts et al, ed. Molecular Biology of the Cell. NY: Garland Publishing, Inc. pp. 346–349, 1983.

Cherng et al. Journal of the Formosan Medical Association. 99(8): 603–611, Aug. 2000.

Neufeld et al. Progress in Growth Factor Research. 5(1): 89–97, 1994.

Gitay–Goren et al. Journal of Biology Chemistry. 271(10)5519–5523, Mar. 1996.

Bio–Critical Synergy: The Biotechnology Industry and Intellectual Property Protection. Hearing of the USPTO, San Diego, CA, Oct. 1994.*

Weich, HA. Accession No. X62568, Jul. 1996.*

Keck et al. Accession No. M27281, Aug. 1994.*

Baird et al. Accession No. Q99081, Q99083, Apr. 1996.*

Fleurbaaij et al. Accession No. T17616, Oct. 1994.*

* cited by examiner

```
-100 AAGAGTAGCTCGCCGAGGCGCCGAGGAGAGGCGGGGCCGCGCCCCACAGCCCGAGCCGGAGAGGAGCGCGAGCCGCGGCCCCCGTCGGCCTCCG

Met Asn Phe Leu Leu Ser Trp Val His Trp Ser Leu Ala Leu Leu Tyr Leu His His Ala Lys
     AAACC ATG AAC TTT CTG CTG TCT TGG GTG CAT TGG AGC CTT GCC CTG CTC TAC CTC CAC CAT GCC AAG gtaag
                                          Exon 1 cggtcgtgccct..........
                *
                            Trp Ser Gln Ala Ala Pro Met Ala Glu Gly Gly Gly Gln Asn His His Glu V
..tctctttctgtcctcag TGG TCC CAG GCT GCA CCC ATG GCA GAA GGA GGA GGG CAG AAT CAT CAC GAA G gtgagt
                                                    Exon 2 al Val Lys Phe Met Asp Val Tyr Gln Arg Ser Tyr Cys His Pro
cccctggctg........catcgcctctcatgcag TG GTG AAG TTC ATG GAT GTC TAT CAG CGC TAC TGC CAT CCA
                                                           Exon 3

Ile Glu Thr Leu Val Asp Ile Phe Gln Glu Tyr Pro Asp Glu Ile Phe Lys Pro Ser Cys Val Pro
ATC GAG ACC CTG GTG GAC ATC TTC CAG GAG TAC CCT GAT GAG ATC TTC AAG CCA TCC TGT GTG CCC

Leu Met Arg Cys Gly Gly Cys Cys Asn Asp Glu Gly Leu Glu Cys Val Pro Thr Glu Ser Asn Ile Thr
CTG ATG CGA TGC GGG GGC TGC TGC AAT GAC GAG GGC CTG GAG TGT GTG CCC ACT GAG TCC AAC ATC ACC

Met Gln                                         Ile Met Arg Ile Lys Pro His Gln Gly Gln His
ATG CAG gtgggcatctttgggaa..........gcttcctccttccag ATT ATG CGG ATC AAA CCT CAC CAA GGC CAG CAC
        Exon 4

Ile Gly Glu Met Ser Phe Met Glu Gln His Leu Asn Lys Cys Glu Cys Ar
ATA GGA GAG ATG AGC TTC ATG GAG CAG CAC CTA AAC AAA TGT GAA TGC AG gtgaggatgtagtcacg g Pro Lys Lys Asp Arg Ala Arg Gln Glu Ly
............ctccctacccattgcag A CCA AAG AAG GAT AGA GCA AGA CAA GAA AA     gtaagtggccct
                              Exon 5
```

FIG 2A

```
                                        s Lys Ser Val Arg Gly Lys Gly Gln Lys Arg Lys Arg Lys Ser
gactt........gttttttatttccag A AAA TCA GTT CGA GGA AAG GGA AAG CAA AAA CGA AAG CGC AAG AAA TCC
                                                        Exon 6a Arg Tyr Lys Ser Trp Ser Va    l Tyr Val Gly Ala Arg Cys Cys Leu Met Pro Trp Ser Leu Pro Gly Pro Hi
CGG TAT AAG TCC TGG AGC GT    G TAC GTT GGT GCC CGC TGC TGT CTA ATG CCC TGG AGC CTC CCT GGC CCC CA....
                                                        Exon 6b s Pro Cys Gly Pro Cys Ser Glu Arg Arg Lys His Leu Phe Val Gln Asp Pro Gln
........cttttgccttttgcag T CCC TGT GGG CCT TGC TCA GAG CGG AGA AAG CAT TTG TTT GTA CAA GAT CCG CAG Thr Cys Lys Cys Ser Cys Lys Asn Thr Asp Ser Arg Cys Lys Ala Arg Gln Leu Glu Leu Asn Glu Arg Thr Cys Ar
ACG TGT AAA TGT TCC TGC AAA AAC ACA GAC TCG CGT TGC AAG GCG AGG CAG CTT GAG TTA AAC GAA CGT ACT TGC AG
                                                        Exon 7 g Cys Asp Lys Pro Arg Arg
gttggttcccagagga.......ttttccatttcccctcag A TGT GAC AAG CCG AGG CGG TGA
                                                        Exon 8

GCCGGGCAGGAGGAAGAGCCTCCCTCAGGGTTTCGGGAACCAGATCTCTCACCAGGAAAGACTGATACAGAACGATCGATACAGAAACCACGCTGCCG
```

FIG. 2B

```
Met Asn Phe Leu Leu Ser Trp Val His Trp Ser Leu Ala Leu Leu Tyr Leu His His Ala Lys
ATG AAC TTT CTG CTG TCT TGG GTG CAT TGG AGC CTT GCC TTG CTC TAC CTC CAC CAT GCC AAG
                                                 Exon 1

*
Trp Ser Gln Ala Ala Pro Met Ala
TGG TCC CAG GCT GCA CCC ATG GCA

Glu Gly Gly Gly Gln Asn His His Glu V
GAA GGA GGA GGG CAG AAT CAT CAC GAA G
 Exon 2                               Exon 3 al Val Lys Phe Met Asp Val Tyr Gln Arg Ser Tyr Cys His Pro Ile Glu Thr Leu
TG GTG AAG TTC ATG GAT GTC TAT CAG CGC AGC TAC TGC CAT CCA ATC GAG ACC CTG

Val Asp Ile Phe Gln Glu Tyr Pro Asp Glu Ile Glu Tyr Ile Phe Lys Pro Ser Cys Val Pro Leu Met Arg Cys Gly
GTG GAC ATC TTC CAG GAG TAC CCT GAT GAG ATC GAG TAC ATC TTC AAG CCA TCC TGT GTG CCC CTG ATG CGA TGC GGG
                                                                                             Exon 5

Gly Cys Cys Asn Asp Gly Leu Glu Cys Val Pro Thr Glu Ser Asn Ile Thr Met Gln Ile Met Arg Ile Lys
GGC TGC TGC AAT GAC GGG CTG GAG TGT GTG CCC ACT GAG AGC AAC ATC ACC ATG CAG ATT ATG CGG ATC AAA
                        Exon 4

Pro His Gln Gly Gln His Ile Gly Glu Met Ser Phe Leu Gln His Asn Lys Cys Leu Met Pro Trp Ser Leu Pro Gly Pro Gl
CCT CAC CAA GGC CAG CAC ATA GGA GAG ATG AGC TTC CTA CAG CAC AAC AAA TGT GAA TGC AG  A CCA AAG AAA GAT AGA
                                                                             Exon 6b Ala Arg Gln Glu Ly    s Tyr Val Gly Ala Arg Cys Cys Leu Met Pro Trp Ser Leu Pro Gly Pro Gl
GCA AGA CAA GAA AA    G TAC GTT GGT GCC CGC TGC TGT CTA ATG CCC TGG AGC CTC CCT GGC CCC CA
                 Exon 6b n Cys Asp Lys Pro Arg Arg
A TGT GAC AAG CCG AGG CGG TGA
 Exon 8
```

FIG 3

```
Met Asn Phe Leu Leu Ser Trp Val His Trp Ser Leu Ala Leu Leu Leu Tyr Leu His His Ala Lys
ATG AAC TTT CTG CTG TCT TGG GTG CAT TGG AGC CTT GCC CTG CTC TAC CTC CAC CAT GCC AAG
                                                                              Exon 1
        *
Trp Ser Gln Ala Ala Pro Met Ala Glu Gly Gly Gln Asn His His Glu V
TGG TCC CAG GCT GCA CCC ATG GCA GAA GGA GGA CAG AAT CAT CAC GAA G
                                                                 Exon 2 al Val Lys Phe Met Asp Val Tyr Gln Arg Ser Tyr Cys His Pro Ile Glu Thr Leu
TG GTG AAG TTC ATG GAT GTC TAT CAG CGC AGC TAC TGC CAT CCA ATC GAG ACC CTG

Val Asp Ile Phe Gln Glu Tyr Pro Asp Glu Ile Phe Lys Pro Ser Cys Val Pro Leu Met Arg Cys Gly Gly
GTG GAC ATC TTC CAG GAG TAC CCT GAT GAG ATC TTC AAG CCA TCC TGT GTG CCC CTG ATG CGA TGC GGG GGC

Cys Cys Asn Asp Glu Gly Leu Glu Cys Val Pro Thr Glu Glu Ser Asn Ile Thr Met Gln     Ile Met Arg Ile Lys Pro His Gln
TGC TGC AAT GAC GAG GGC CTG GAG TGT GTG CCC ACT GAG GAG TCC AAC ATC ACC ATG CAG     ATT ATG CGG ATC AAA CCT CAC CAA
                                                  Exon 3

Gly Gln His Ile Gly Glu Met Ser Phe Leu Gln His Asn Lys Cys Glu Cys Ar   g Pro Lys Lys Asp Arg Ala Arg Gln Glu Ly
GGC CAG CAC ATA GGA GAG ATG AGC TTC CTA CAG CAC AAC AAA TGT GAA TGC AG   A CCA AAG AAA GAT AGA GCA AGA CAA GAA AA
                                     Exon 4                                                              Exon 5 s Tyr Val Gly Ala Arg Cys Cys Leu Met Pro Trp Ser Leu Pro Gly Pro Hi   s Pro Cys Gly Pro Cys Ser Glu Arg Arg Lys
G TAC GTT GGT GCC CGC TGC TGT CTA ATG CCC TGG AGC CTC CCT GGC CCC CA   T CCC TGT GGG CCT TGC TCA GAG CGG AGA AAG
                         Exon 6b His Leu Phe Val Gln Asp Pro Gln Thr Cys Lys Cys Ser Cys Lys Asn Thr Asp Ser Arg Cys Lys Ala Arg Gln Leu Glu Leu
CAT TTG TTT GTA CAA GAT CCG CAG ACG TGT AAA TGT TCC TGC AAA AAC ACA GAC TCG CGT TGC AAG GCG AGG CAG CTT GAG TTA Asn Glu Arg Thr Cys Ar   g Cys Asp Lys Pro Arg Arg
AAC GAA CGT ACT TGC AG   A TGT GAC AAG CCG AGG CGG TGA
      Exon 7                        Exon 8
```

FIG 4

```
Met Asn Phe Leu Leu Ser Trp Val His Trp Ser Leu Ala Leu Leu Tyr Leu His His Ala Lys
ATG AAC TTT CTG CTG TCT TGG GTG CAT TGG AGC CTT GCC CTG CTC TAC CTC CAC CAT GCC AAG
                                    Exon 1
                *
Trp Ser Gln Ala Ala Pro Met Ala Glu Gly Gly Gln Asn His His Glu V    al Val Lys Phe Met Asp Val Tyr Gln Arg
TGG TCC CAG GCT GCA CCC ATG GCA GAA GGA GGG CAG AAT CAT CAC GAA G    TG GTG AAG TTC ATG GAT GTC TAT CAG CGC
                            Exon 2

Ser Tyr Cys His Pro Ile Glu Thr Leu Val Asp Ile Phe Gln Glu Tyr Pro Asp Glu Ile Glu Tyr Ile Phe Lys Pro Ser
AGC TAC TGC CAT CCA ATC GAG ACC CTG GTG GAC ATC TTC CAG GAG TAC CCT GAT GAG ATC GAG TAC ATC TTC AAG CCA TCC
                                                Exon 3

Cys Val Pro Leu Met Arg Cys Gly Gly Cys Cys Asn Asp Glu Gly Leu Glu Cys Val Pro Thr Glu Glu Ser Asn Ile Thr
TGT GTG CCC CTG ATG CGA TGC GGG GGC TGC TGC AAT GAC GAG GGC CTG GAG TGT GTG CCC ACT GAG GAG TCC AAC ATC ACC

Met Gln     Ile Met Arg Ile Lys Pro His Gln Gly Gln His Ile Gly Glu Met Ser Phe Leu Gln His Asn Lys Cys
ATG CAG     ATT ATG CGG ATC AAA CCT CAC CAA GGC CAG CAT ATA GGA GAG ATG AGC TTC CTA CAG CAC AAC AAA TGT
                                                    Exon 4

Glu Cys Ar    g Pro Lys Lys Asp Arg Ala Arg Gln Glu Ly
GAA TGC AG    A CCA AAG AAA GAT AGA GCA AGA CAA GAA AA
                            Exon 5 s Lys Ser Val Arg Gly Lys Gly Lys Gly Gln Lys Arg Lys Arg Lys Lys Ser Arg Tyr Lys Ser Trp Ser Va
A AAA TCA GTT CGA GGA AAG GGA AAG GGA CAA AAA CGA AAG AGA AAG CGC AAG AAA TCC CGG TAT AAG TCC TGG AGC GT
                                    Exon 6a l Tyr Val Gly Ala Arg Cys Cys Leu Met Pro Trp Ser Leu Pro Gly Pro Gl    n Cys Asp Lys Pro Arg Arg
G TAC GTT GGT GCC CGC TGT TGT CTA ATG CCC TGG AGC CTC CCT GGC CCC CA    A TGT GAC AAG CCG AGG CGG TGA
                        Exon 6b                                                    Exon 8

GCCGGGCAGGAGGAAGGAGCCTCCCTCAGGGTTTCGGAACCAGATCTCTCACCAGGAAAGACTGATACAGAACGATCGATACAGAAACCACGCTGCCG
```

FIG 5

SEQUENCE LISTING

<160> NUMBER OF SEQ ID NOS: 29

<210> SEQ ID NO 1
<211> LENGTH: 545
<212> TYPE: DNA
<213> ORGANISM: Homo sapien

<400> SEQUENCE: 1

```
ggatccgaaa ccatgaactt tctgctgtct tgggtgcatt ggagccttgc cttgctgctc      60
tacctccacc atgccaagtg gtcccaggct gcacccatgg cagaaggagg agggcagaat     120
catcacgaag tggtgaagtt catggatgtc tatcagcgca gctactgcca tccaatcgag     180
```

```
acccctggtgg acatcttcca ggagtaccct gatgagatcg agtacatctt caagccatcc    240
tgtgtgcccc tgatgcgatg cggggggctgc tgcaatgacg agggcctgga gtgtgtgccc    300
actgaggagt ccaacatcac catgcagatt atgcggatca aacctcacca aggccagcac    360
ataggagaga tgagcttcct acagcacaac aaatgtgaat gcagaccaaa gaaagataga    420
gcaagacaag aaaaaaaatc agttcgagga aagggaaagg ggcaaaaacg aaagcgcaag    480
aaatcccggt ataagtcctg gagcgtatgt gacaagccga ggcggtgatg aatgaatgag    540
gatcc                                                                545

<210> SEQ ID NO 2
<211> LENGTH: 51
<212> TYPE: DNA
<213> ORGANISM: Homo sapien

<400> SEQUENCE: 2
gtacgttggt gcccgctgct gtctaatgcc ctggagcctc cctggccccc a              51

<210> SEQ ID NO 3
<211> LENGTH: 29
<212> TYPE: DNA
<213> ORGANISM: Artificial Sequence
<220> FEATURE:
<223> OTHER INFORMATION: artificially synthesized sequence for PCR
      synthesis, containing a portion of human VEGF-A sequence.
<220> FEATURE:
<223> OTHER INFORMATION: "n" stands for a, g, c or t.

<400> SEQUENCE: 3
nnnnnntacg tacgttggtg cccgctgct                                       29

<210> SEQ ID NO 4
<211> LENGTH: 29
<212> TYPE: DNA
<213> ORGANISM: Artificial Sequence
<220> FEATURE:
<223> OTHER INFORMATION: artificially synthesized sequence for PCR
      synthesis, containing a portion of human VEGF-A sequence.
<220> FEATURE:
<223> OTHER INFORMATION: "n" stands for a, g, c or t.

<400> SEQUENCE: 4
acctcggagg gaccgggggc cctatagnn                                       29

<210> SEQ ID NO 5
<211> LENGTH: 69
<212> TYPE: DNA
<213> ORGANISM: Artificial Sequence
<220> FEATURE:
<223> OTHER INFORMATION: artificially synthesized sequence containing a
      portion of human VEGF-A Exon 6b.
<220> FEATURE:
<223> OTHER INFORMATION: "n" stands for a, g, c or t.

<400> SEQUENCE: 5
nnnnnntacg tacgttggtg cccgctgctg tctaatgccc tggagcctcc ctggccccg      60 ggatatcnn                                                             69

<210> SEQ ID NO 6
<211> LENGTH: 54
<212> TYPE: DNA
<213> ORGANISM: Homo sapien

<400> SEQUENCE: 6
```

-continued aatgtgacaa gccgaggcgg tgatgaatga atgaggatgc ggccgcaaaa ggaa 54

<210> SEQ ID NO 7
<211> LENGTH: 20
<212> TYPE: DNA
<213> ORGANISM: Cauliflower Mosaic Virus

<400> SEQUENCE: 7
gcagagctcg tttagtgaac 20

<210> SEQ ID NO 8
<211> LENGTH: 22
<212> TYPE: PRT
<213> ORGANISM: Homo sapien

<400> SEQUENCE: 8

Met Asn Phe Leu Leu Ser Trp Val His Trp Ser Leu Ala Leu Leu Leu
1               5                   10                  15

Tyr Leu His His Ala Lys
            20

<210> SEQ ID NO 9
<211> LENGTH: 183
<212> TYPE: DNA
<213> ORGANISM: Homo sapien

<400> SEQUENCE: 9
aagagtagct cgccgaggcg ccgaggagag cgggccgccc acagcccga gccggagagg 60 gagcgcgagc cgcgccggcc ccgtcgggc ctccgaaacc atgaactttc tgctgtcttg 120
ggtgcattgg agccttgcct tgctgctcta cctccaccat gccaaggtaa gcggtcgtgc 180
cct 183

<210> SEQ ID NO 10
<211> LENGTH: 17
<212> TYPE: PRT
<213> ORGANISM: Homo sapien

<400> SEQUENCE: 10

Trp Ser Gln Ala Ala Pro Met Ala Glu Gly Gly Gln Asn His His
1               5                   10                  15

Glu

<210> SEQ ID NO 11
<211> LENGTH: 86
<212> TYPE: DNA
<213> ORGANISM: Homo sapien

<400> SEQUENCE: 11
tctctttctg tcctcagtgg tcccaggctg cacccatggc agaaggagga gggcagaatc 60
atcacgaagg tgagtccccc tggctg 86

<210> SEQ ID NO 12
<211> LENGTH: 65
<212> TYPE: PRT
<213> ORGANISM: Homo sapien

<400> SEQUENCE: 12

Val Lys Phe Met Asp Val Tyr Gln Arg Ser Tyr Cys His Pro Ile Glu
1               5                   10                  15

```
Thr Leu Val Asp Ile Phe Gln Glu Tyr Pro Asp Glu Ile Glu Tyr Ile
         20                  25                  30

Phe Lys Pro Ser Cys Val Pro Leu Met Arg Cys Gly Cys Cys Asn
         35                  40                  45

Asp Glu Gly Leu Glu Cys Val Pro Thr Glu Glu Ser Asn Ile Thr Met
 50                      55                  60

Gln
 65

<210> SEQ ID NO 13
<211> LENGTH: 231
<212> TYPE: DNA
<213> ORGANISM: Homo sapien

<400> SEQUENCE: 13
catcgcctct catgcagtgg tgaagttcat ggatgtctat cagcgcagct actgccatcc      60
aatcgagacc ctggtggaca tcttccagga gtaccctgat gagatcgagt acatcttcaa    120
gccatcctgt gtgcccctga tgcgatgcgg gggctgctgc aatgacgagg gcctggagtg    180
tgtgcccact gaggagtcca acatcaccat gcaggtgggc atctttggga a              231

<210> SEQ ID NO 14
<211> LENGTH: 25
<212> TYPE: PRT
<213> ORGANISM: Homo sapien

<400> SEQUENCE: 14

Ile Met Arg Ile Lys Pro His Gln Gly Gln His Ile Gly Glu Met Ser
 1               5                  10                  15

Phe Leu Gln His Asn Lys Cys Glu Cys
         20                  25

<210> SEQ ID NO 15
<211> LENGTH: 111
<212> TYPE: DNA
<213> ORGANISM: Homo sapien

<400> SEQUENCE: 15
gcttccttcc tttccagatt atgcggatca aacctcacca aggccagcac ataggagaga     60
tgagcttcct acagcacaac aaatgtgaat gcaggtgagg atgtagtcac g             111

<210> SEQ ID NO 16
<211> LENGTH: 9
<212> TYPE: PRT
<213> ORGANISM: Homo sapien

<400> SEQUENCE: 16

Pro Lys Lys Asp Arg Ala Arg Gln Glu
 1               5

<210> SEQ ID NO 17
<211> LENGTH: 64
<212> TYPE: DNA
<213> ORGANISM: Homo sapien

<400> SEQUENCE: 17
ctccctaccc attgcagacc aaagaaagat agagcaagac aagaaaagta agtggccctg     60
actt                                                                  64

<210> SEQ ID NO 18
```

-continued

```
<211> LENGTH: 40
<212> TYPE: PRT
<213> ORGANISM: Homo sapien

<400> SEQUENCE: 18

Lys Ser Val Arg Gly Lys Gly Lys Gly Gln Lys Arg Lys Arg Lys Lys
 1               5                  10                  15

Ser Arg Tyr Lys Ser Trp Ser Val Tyr Val Gly Ala Arg Cys Cys Leu
            20                  25                  30

Met Pro Trp Ser Leu Pro Gly Pro
            35                  40

<210> SEQ ID NO 19
<211> LENGTH: 140
<212> TYPE: DNA
<213> ORGANISM: Homo sapien

<400> SEQUENCE: 19 gttttttat   tttccagaaa   atcagttcga   ggaaagggaa   aggggcaaaa   acgaaagcgc     60
aagaaatccc  ggtataagtc   ctggagcgtg   tacgttggtg   cccgctgctg   tctaatgccc    120
tggagcctcc  ctggccccca                                                        140

<210> SEQ ID NO 20
<211> LENGTH: 43
<212> TYPE: PRT
<213> ORGANISM: Homo sapien

<400> SEQUENCE: 20

Pro Cys Gly Pro Cys Ser Glu Arg Arg Lys His Leu Phe Val Gln Asp
 1               5                  10                  15

Pro Gln Thr Cys Lys Cys Ser Cys Lys Asn Thr Asp Ser Arg Cys Lys
            20                  25                  30

Ala Arg Gln Leu Glu Leu Asn Glu Arg Thr Cys
            35                  40

<210> SEQ ID NO 21
<211> LENGTH: 166
<212> TYPE: DNA
<213> ORGANISM: Homo sapien

<400> SEQUENCE: 21
cttttgcctt   tttgcagtcc   ctgtgggcct   tgctcagagc   ggagaaagca   tttgtttgta     60
caagatccgc   agacgtgtaa   atgttcctgc   aaaaacacag   actcgcgttg   caaggcgagg    120
cagcttgagt   taaacgaacg   tacttgcagg   ttggttccca   gaggca                    166

<210> SEQ ID NO 22
<211> LENGTH: 6
<212> TYPE: PRT
<213> ORGANISM: Homo sapien

<400> SEQUENCE: 22

Cys Asp Lys Pro Arg Arg
 1               5

<210> SEQ ID NO 23
<211> LENGTH: 138
<212> TYPE: DNA
<213> ORGANISM: Homo sapien

<400> SEQUENCE: 23
```

-continued

```
ttttccattt ccctcagatg tgacaagccg aggcggtgag ccgggcagga ggaaggagcc        60
tccctcaggg tttcgggaac cagatctctc accaggaaag actgatacag aacgatcgat       120
acagaaacca cgctgccg                                                     138
```

<210> SEQ ID NO 24
<211> LENGTH: 164
<212> TYPE: PRT
<213> ORGANISM: Homo sapien

<400> SEQUENCE: 24

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Tyr Val Gly
    130                 135                 140

Ala Arg Cys Cys Leu Met Pro Trp Ser Leu Pro Gly Pro Gln Cys Asp
145                 150                 155                 160

Lys Pro Arg Arg
```

<210> SEQ ID NO 25
<211> LENGTH: 495
<212> TYPE: DNA
<213> ORGANISM: Homo sapien

<400> SEQUENCE: 25

```
atgaactttc tgctgtcttg ggtgcattgg agccttgcct tgctgctcta cctccaccat        60
gccaagtggt cccaggctgc acccatggca gaaggaggag gcagaatca tcacgaagtg       120 gtgaagttca tggatgtcta tcagcgcagc tactgccatc caatcgagac cctggtggac       180
atcttccagg agtaccctga tgagatcgag tacatcttca agccatcctg tgtgcccctg       240
atgcgatgcg ggggctgctg caatgacgag ggcctggagt gtgtgcccac tgaggagtcc       300
aacatcacca tgcagattat gcggatcaaa cctcaccaag ccagcacat aggagagatg       360 agcttcctac agcacaacaa atgtgaatgc agaccaaaga agatagagc aagcaagaa       420 aagtacgttg gtgcccgctg ctgtctaatg ccctggagcc tccctggccc ccaatgtgac       480
aagccgaggc ggtga                                                        495
```

<210> SEQ ID NO 26
<211> LENGTH: 208
<212> TYPE: PRT
<213> ORGANISM: Homo sapien

<400> SEQUENCE: 26

```
Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Tyr Val Gly
    130                 135                 140

Ala Arg Cys Cys Leu Met Pro Trp Ser Leu Pro Gly Pro His Pro Cys
145                 150                 155                 160

Gly Pro Cys Ser Glu Arg Arg Lys His Leu Phe Val Gln Asp Pro Gln
                165                 170                 175

Thr Cys Lys Cys Ser Cys Lys Asn Thr Asp Ser Arg Cys Lys Ala Arg
            180                 185                 190

Gln Leu Glu Leu Asn Glu Arg Thr Cys Arg Cys Asp Lys Pro Arg Arg
        195                 200                 205

<210> SEQ ID NO 27
<211> LENGTH: 627
<212> TYPE: DNA
<213> ORGANISM: Homo sapien

<400> SEQUENCE: 27
atgaactttc tgctgtcttg ggtgcattgg agccttgcct tgctgctcta cctccaccat      60
gccaagtggt cccaggctgc acccatggca gaaggaggag gcagaatcac atcacgaagtg    120 gtgaagttca tggatgtcta tcagcgcagc tactgccatc caatcgagac cctggtggac    180
atcttccagg agtaccctga tgagatcgag tacatcttca agccatcctg tgtgcccctg    240
atgcgatgcg ggggctgctg caatgacgag ggcctggagt gtgtgcccac tgaggagtcc    300
aacatcacca tgcagattat gcggatcaaa cctcaccaag ccagcacat aggagagatg      360 agcttcctac agcacaacaa atgtgaatgc agaccaaaga agatagagc aagacaagaa       420 aagtacgttg gtgcccgctg ctgtctaatg ccctggagcc tcctggccc ccatccctgt       480 gggccttgct cagagcggag aaagcatttg tttgtacaag atccgcagac gtgtaaatgt     540
tcctgcaaaa acacagactc gcgttgcaag gcgaggcagc ttgagttaaa cgaacgtact    600
tgcagatgtg acaagccgag gcggtga                                         627

<210> SEQ ID NO 28
<211> LENGTH: 188
<212> TYPE: PRT
<213> ORGANISM: Homo sapien

<400> SEQUENCE: 28

Met Asn Phe Leu Leu Ser Trp Val His Trp Ser Leu Ala Leu Leu Leu
```

```
  1               5                    10                    15
Tyr Leu His His Ala Lys Trp Ser Gln Ala Ala Pro Met Ala Glu Gly
            20                  25              30

Gly Gly Gln Asn His His Glu Val Val Lys Phe Met Asp Val Tyr Gln
            35              40                  45

Arg Ser Tyr Cys His Pro Ile Glu Thr Leu Val Asp Ile Phe Gln Glu
 50                     55                  60

Tyr Pro Asp Glu Ile Glu Tyr Ile Phe Lys Pro Ser Cys Val Pro Leu
 65                 70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
            130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro Gln Cys Asp Lys Pro Arg Arg
            180                 185
```

<210> SEQ ID NO 29
<211> LENGTH: 665
<212> TYPE: DNA
<213> ORGANISM: Homo sapien

<400> SEQUENCE: 29

```
atgaactttc tgctgtcttg ggtgcattgg agccttgcct tgctgctcta cctccaccat    60
gccaagtggt cccaggctgc acccatggca gaaggaggag ggcagaatca tcacgaagtg   120
gtgaagttca tggatgtcta tcagcgcagc tactgccatc caatcgagac cctggtggac   180
atcttccagg agtaccctga tgagatcgag tacatcttca agccatcctg tgtgcccctg   240
atgcgatgcg ggggctgctg caatgacgag ggcctggagt gtgtgcccac tgaggagtcc   300
aacatcacca tgcagattat gcggatcaaa cctcaccaag ccagcacat aggagagatg   360 agcttcctac agcacaacaa atgtgaatgc agaccaaaga agatagagc aagacaagaa   420 aaaaaatcag ttcgaggaaa gggaaagggg caaaaacgaa agcgcaagaa atcccggtat   480
aagtcctgga gcgtgtacgt tggtgcccgc tgctgtctaa tgccctggag cctccctggc   540
ccccaatgtg acaagccgag gcggtgaccg ggcaggagga aggagcctcc ctcagggttt   600
cgggaaccag atctctcacc aggaaagact gatacagaac gatcgataca gaaaccacgc   660
tgccg                                                              665
```

FORMS OF THE ANGIOGENIC FACTOR VASCULAR ENDOTHELIAL CELL GROWTH FACTOR: VEGF

This application claims priority to Provisional Application Baird, et al., U.S. Ser. No. 60/073,979, filed Feb. 6, 1998, entitled NOVEL FORMS OF THE ANGIOGENIC FACTOR VASCULAR ENDOTHELIAL CELL GROWTH FACTOR: VEGF.

FIELD OF THE INVENTION

The present invention relates to novel forms of vascular endothelial growth factor genes and the novel proteins encoded by these genes. More particularly, the invention relates to novel forms of human VEGF-A. These novel forms of VEGF-A include VEGF-$A_{138}$, VEGF-$A_{162}$, and VEGF-$A_{182}$. Such novel VEGF proteins may be used in the treatment of the cardiovascular system and its diseases through effects on anatomy, conduit function, and permeability, and more particularly in the treatment of cardiovascular disease by stimulating vascular cell proliferation using a growth factor, thereby stimulating endothelial cell growth and vascular permeability.

The invention also relates to nucleic acids encoding such novel VEGF proteins, cells, tissues and animals containing such nucleic acids; methods of treatment using such nucleic acids; and methods relating to all of the foregoing.

BACKGROUND OF THE INVENTION

Cardiovascular diseases are generally characterized by an impaired supply of blood to the heart or other target organs. Myocardial infarction (MI), commonly referred to as heart attacks, is a leading cause of mortality as 30% are fatal in the first months following the heart attack. Heart attacks result from narrowed or blocked coronary arteries in the heart which starves the heart of needed nutrients and oxygen. When the supply of blood to the heart is compromised, cells respond by generating compounds that induce the growth of new blood vessels so as to increase the supply of blood to the heart. These new blood vessels are called collateral blood vessels. The process by which new blood vessels are induced to grow out of the existing vasculature is termed angiogenesis, and the substances that are produced by cells to induce angiogenesis are the angiogenic factors.

Unfortunately, the body's natural angiogenic response is limited and often inadequate. For this reason, the discovery of angiogenic growth factors has lead to the emergence of an alternative therapeutic strategy which seeks to supplement the natural angiogenic response by supplying exogenous angiogenic substances.

Attempts have been made to stimulate angiogenesis by administering various growth factors. U.S. Pat. No. 5,318,957 to Cid et al. discloses a method of stimulating angiogenesis by administering haptoglobins (glyco-protein with two polypeptide chains linked by disulfide bonds). Intracoronary injection of a recombinant vector expressing human fibroblast growth factor-5 (FGF-5) (i.e., in vivo gene transfer) in an animal model resulted in successful amelioration of abnormalities in myocardial blood flow and function. (Giordano, F. J., et. al. *Nature Med* 2, 534–539, 1996). Recombinant adenoviruses have also been used to express angiogenic growth factors in-vivo. These included acidic fibroblast growth factor (Muhlhauser, J., et. al. *Hum. Gene Ther.* 6:1457–1465, 1995), and one of the VEGF forms, VEGF-$A_{165}$ (Muhlhauser, J., et. al. *Circ. Res.* 77:1077–1086, 1995).

One of the responses of heart muscle cells to impaired blood supply involves activation of the gene encoding Vascular Endothelial Growth Factor ("VEGF"), also known as VEGF-A, (Banai, S., et. al. *Cardiovasc. Res.* 28:1176–1179, 1994). VEGF-A is actually a family of angiogenic factors that induce the growth of new collateral blood vessels. These growth factors are specific angiogenic growth factors that have vaso-permeability activity and target endothelial (blood vessel-lining) cells almost exclusively. (Reviewed in Ferrara et al., *Endocr. Rev.* 13:18–32 (1992); Dvorak et al., *Am. J. Pathol.* 146:1029–39 (1995); Thomas, *J. Biol. Chem.* 271:603–06 (1996)). Expression of the VEGF-A gene is linked in space and time to events of physiological angiogenesis, and deletion of the VEGF-A gene by way of targeted gene disruption in mice leads to embryonic death because the blood vessels do not develop. It is therefore the only known angiogenic growth factor that appears to function as a specific physiological regulator of angiogenesis.

When tested in cell culture, VEGF-A, and, because of its structure, likely VEGF-B, (VEGF's) are potently mitogenic (Gospodarowicz et al., *Proc. Natl. Acad. Sci. USA* 86:7311–15, 1989) and chemotactic (Favard et al., *Biol. Cell* 73:1–6, 1991). Additionally, VEGFs induce plasminogen activator, plasminogen activator inhibitor, and plasminogen activator receptor (Mandriota et al., *J. Biol. Chem.* 270:9709–16, 1995; Pepper et al., 181: 902–06, 1991), as well as collagenases (Unemori et al., *J. Cell. Physiol.* 153:557–62, 1992), enzyme systems that regulate invasion of growing capillaries into tissues. VEGFs also stimulate the formation of tube-like structures by endothelial cells, an in vitro example of angiogenesis (Nicosia et al., *Am. J. Pathol.*, 145:1023–29, 1994).

In vivo, VEGFs induce angiogenesis (Leung et al., *Science* 246:1306–09, 1989) and increase vascular permeability (Senger et al., *Science* 219:983–85, 1983). VEGFs are now known as important physiological regulators of capillary blood vessel formation. They are involved in the normal formation of new capillaries during organ growth, including fetal growth (Peters et al., *Proc. Natl. Acad. Sci. USA* 90:8915–19, 1991), tissue repair (Brown et al., *J. Exp. Med.* 176:1375–79, 1992), the menstrual cycle, and pregnancy (Jackson et al., *Placenta* 15:341–53, 1994; Cullinan & Koos, *Endocrinology* 133:829–37, 1993; Kamat et al., *Am. J. Pathol.* 146:157–65, 1995). During fetal development, VEGFs appear to play an essential role in the de novo formation of blood vessels from blood islands (Risau & Flamme, *Ann. Rev. Cell. Dev. Biol.* 11:73–92, 1995), as evidenced by abnormal blood vessel development and lethality in embryos lacking a single VEGF allele (Carmeliet et al., *Nature* 380:435–38, 1996). Moreover, VEGFs are implicated in the pathological blood vessel growth characteristic of many diseases, including solid tumors (Potgens et al., *Biol. Chem. Hoppe-Seyler* 376:57–70, 1995), retinopathies (Miller et al., *Am. J. Pathol.* 145:574–84, 1994; Aiello et al., *N. Engl. J. Med.* 331:1480–87, 1994; Adamis et al., *Am. J. Ophthalmol.* 118:445–50, 1994), psoriasis (Detmar et al., *J. Exp. Med.* 180:1141–46, 1994), and rheumatoid arthritis (Fava et al., *J. Exp. Med.* 180:141–46, 1994).

VEGF expression is regulated by hormones (Schweiki et al., *J. Clin. Invest.* 91:2235–43, 1993) growth factors (Thomas, *J. Biol. Chem.* 271:603–06, 1996), and by hypoxia (Schweiki et al., *Nature* 359:843–45, 1992, Levy et al., *J. Biol. Chem.* 271:2746–53, 1996). Upregulation of VEGFs by hypoxic conditions is of particular importance as a compensatory mechanism by which tissues increase oxygenation through induction of additional capillary vessel formation and resulting increased blood flow. This mechanism is thought to contribute to pathological angiogenesis in tumors and in retinopathies. However, upregulation of VEGF expression after hypoxia is also essential in tissue repair, e.g., in dermal wound healing (Frank et al., *J. Biol. Chem.* 270:12607–613, 1995), and in coronary ischemia (Banai et al., *Cardiovasc. Res.* 28:1176–79, 1994; Hashimoto et al., *Am. J. Physiol.* 267:H1948-H1954, 1994).

Using the rabbit chronic limb ischemia model, it has been shown that repeated intramuscular injection or a single intra-arterial bolus of VEGF-A can augment collateral blood vessel formation as evidenced by blood flow measurement in the ischemic hindlimb (Pu, et al., *Circulation* 88:208–15, 1993; Bauters et al., *Am. J. Physiol.* 267:HI263-71, 1994; Takeshita et al., *Circulation* 90 [part 2], II-228–34, 1994; Bauters et al.,*J. Vasc. Surg.* 21:314–25, 1995; Bauters et al., *Circulation* 91:2802–09, 1995; Takeshita et al., *J. Clin. Invest.* 93:662–70, 1994). In this model, VEGF has also been shown to act synergistically with basic FGF to ameliorate ischemia (Asahara et al., *Circulation* 92:[suppl 2], II-365–71, 1995). VEGF was also reported to accelerate the repair of balloon-injured rat carotid artery endothelium while at the same time inhibiting pathological thickening of the underlying smooth muscle layers, thereby maintaining lumen diameter and blood flow (Asahara et al., *Circulation* 91:2793–2801, 1995). VEGF has also been shown to induce EDRF (Endothelin-Derived Relaxin Factor (nitric oxide))-dependent relaxation in canine coronary arteries, thus potentially contributing to increased blood flow to ischemic areas via a secondary mechanism not related to angiogenesis (Ku et al., *Am. J. Physiol* 265:H586-H592, 1993).

Activation of the gene encoding VEGF-A results in the production of several different VEGF-A variants, or isoforms, produced by alternative splicing wherein the same chromosomal DNA yields different mRNA transcripts containing different exons thereby producing different proteins. Such variants have been disclosed, for example, in U.S. Pat. No. 5,194,596 to Tischer et al. which identifies human vascular endothelial cell growth factors having peptide sequence lengths of 121, and 165 amino acids (i.e., VEGF-$A_{121}$ and VEGF-$A_{165}$). Additionally, VEGF-$A_{189}$ and VEGF-$A_{206}$ have also been characterized and reported (Neufeld, G., et. al. *Cancer Metastasis Rev.* 15:153–158, 1996).

The mitogenic activity of the various VEGF-A isoforms varies depending on each isoform. For example, VEGF-$A_{121}$ and VEGF-$A_{165}$ have very similar mitogenic activity for endothelial cells. However, VEGF-$A_{189}$ and VEGF-$A_{206}$ are only weakly mitogenic (Ferrara et al., *Endocr. Rev.* 13:18–32, 1992). The reduced activity of these isoforms is attributed to their strong association with cells and matrix, as evidenced by the normal mitogenic activity of a mutant of VEGF-$A_{206}$ which lacks the 24-residue "matrix targeting" sequence common to VEGF-$A_{189}$ and VEGF-$A_{206}$ (residues 115–139 in FIG. 2) (Ferrara et al., *Endocr. Rev.* 13:18–32, 1992).

Four known forms of VEGF-A arise from alternative splicing of up to eight exons of the VEGF-A gene (VEGF-$A_{121}$, exons 1–5, 8; VEGF-$A_{165}$, exons 1–5,7,8; VEGF-$A_{189}$, exons 1–5, 6a, 7, 8; VEGF-$A_{206}$, exons 1–5, 6a, 6b, 7, 8 (exon 6a and 6b refer to 2 alternatively spliced forms of the same exon)) (Houck et al., *Mol. Endocr.,* 5:1806–14 (1991)). All VEGF-A genes encode signal peptides that direct the protein into the secretary pathway. For example, VEGF-$A_{165}$ cDNA encodes a 191-residue amino acid sequence consisting, of a 26-residue secretary signal peptide sequence, which is cleaved upon secretion of the protein from cells, and the 165-residue mature protein subunit. However, only VEGF-$A_{121}$ and VEGF-$A_{165}$ are found to be readily secreted by cultured cells whereas VEGF-$A_{189}$ and VEGF-$A_{206}$ remain associated with the producing cells. These VEGF-A forms possess an additional highly basic sequence encoded by exon 6 corresponding to residues 115–139 in VEGF-$A_{189}$ and residues 115–156 in VEGF-$A_{206}$. These additions confer a high affinity to heparin and an ability to associate with the extracellular matrix (matrix-targeting sequence) (Houck, K. A. et al., *J. Biol. Chem.* 267:26031–37 (1992) and Thomas, *J. Biol. Chem,* 271:603–06 (1996)). The mitogenic activities of VEGF-$A_{121}$ and VEGF-$A_{165}$ are similar according to the results of several groups (Neufeld, G., et al., *Cancer Metastasis Rev.* 15:153–158 (1996) although one research group has shown evidence indicating that VEGF-$A_{121}$ is significantly less active (Keyt, B. A., et al. *J. Biol. Chem.* 271:7798–7795 (1996). It is unclear whether the two longer VEGF-A forms, VEGF-$A_{189}$ and VEGF-$A_{206}$, are as active or less active than the two shorter forms since it has not been possible to obtain them in pure form suitable for quantitative measurements. This failure is due in part to their strong association with producing cells and extracellular matrices which is impaired by the presence of exon-6 derived sequences apparently acting in synergism with exon-7 derived sequences groups (Neufeld, G., et al., *Cancer Metastasis Rev.* 15:153–158 (1996).

As depicted in FIG. 1, the domain encoded by exons 1–5 contains information required for the recognition of the VEGF receptors flt-1 ($R_1$ and $R_2$) and KDR/flk-1 (Keyt, B. A., et. al. *J. Biol Chem* 271:5638–5646, 1996), and is present in all known VEGF isoforms. The amino-acids encoded by exon 8 are also present in all known isoforms. The isoforms may be distinguished however by the presence or absence of the peptides encoded by exons 6 and 7 of the VEGF-A gene, and the presence or absence of the peptides encoded by these exons results in structural differences which are translated into functional differences between the VEGF-A forms (reviewed in: Neufeld, G., et. al. *Cancer Metastasis Rev.* 15, 153–158. 1996).

Exon 6 can terminate after 72 bp at a donor splice site wherein it contributes 24 amino acids to VEGF forms that contain it such as VEGF-$A_{189}$. This exon 6 form is referred to herein as exon 6a. However, the VEGF-A RNA can be spliced at the 3' end of exon 6 using an alternative splice site located 51 bp downstream to the first resulting in a larger exon 6 product containing 41 amino-acids. The additional 17 amino-acids added to the exon 6 product as a result of this alternative splicing are referred to herein as exon 6b. VEGF-$A_{206}$ contains the elongated exon 6 composed of 6a and 6b, but this VEGF form is much rarer than VEGF-$A_{189}$. (Tischer, E., et al.,*J. Biol. Chem.* 266, 11947–11954; Houck, K. A., et al., *Mol. Endocrinol.,* 1806–1814, 1991).

A putative fifth form of VEGF-A, VEGF-$A_{145}$, has been noted in the human endometrium, using PCR. The authors state that the sequence of the cDNA of the VEGF-$A_{145}$ splice variant indicated that it contained exons 1–5, 6 and 8. However, it is uncertain whether the authors found that the splice variant contained exons 6a and 6b as in VEGF-$A_{206}$, exon 6a as in VEGF-$A_{189}$, or exon 6b. The authors state that since the splice variant retains exon 6 it is probable that it will be retained by the cell as are the other members of the family that contain this exon. (Charnock-Jones et al., *Biology of Reproduction* 48, 1120–1128 (1993); see also, Bacic M., et al. *Growth Factors* 12, 11–15, 1995). The biologic activity of this form was not established in that report (Cheung, C. Y., et al., *Am. J. Obstet. Gynecol.,* 173, 751–759, 1995); Anthony, F. W. et al., *Placenta*, 15, 557–561, 1994). The various isoforms, and the exons that encode the isoforms, are depicted in FIG. 1.

More recently, a VEGF-A protein of 145 amino acids, and nucleic acid encoding this protein, have been identified, and its use for treating the cardiovascular system and its diseases has been identified (U.S. Ser. No. 08/784,551 now U.S. Pat. No. 6,013,780, filed Jan. 21, 1997, published as WO 98/10071 on Mar. 12, 1998).

VEGF-A is known to bind to two of three different endothelial cell receptors, each of which is a single transmembrane protein with a large extracellular portion comprised of 7 immunoglobulin-type domains and a cytoplasmic portion that functions as a tyrosine kinase. These receptors are $R_1$ (flt-1) (De Vries et al., *Science* 255:989–91, 1992), $R_2$ (KDR/flk-1) (Terman et al., *Biochem. Biophys. Res. Commun.* 187:1579–86, 1992), and $R_3$ (flk-4) (Pajusola et al., *Cancer Res.* 52:5738–43, 1992). There are distinct selectivities between these receptors and the various VEGF-A and VEGF-related protein ligands that have not been completely elucidated as yet. However, it is known that VEGF-A binds to $R_1$ and R2 (Terman et al., *Growth Factors* 11:187–95, 1994) but not $R_3$ (Joukov et al., *EMBO J.* 15:290–98, 1996). $R_2$ is thought to be primarily responsible for the angiogenic response of endothelial cells to VEGF-like growth factors (Gitay-Goren et al., *J. Biol. Chem.* 271:5519–23 (1996)).

Accordingly, there is a need for new forms of VEGF-A proteins that have modified affinities for matrix and low affinity receptor. This modified affinity will alter its bioavailability when administered.

SUMMARY OF THE INVENTION

The present invention is directed to novel forms of VEGF proteins, preferably human VEGF-A proteins. The preferred use of the VEGF proteins and nucleic acid molecule compositions of the invention is to use such compositions to treat the cardiovascular system and its diseases through effects on anatomy, conduit function, and permeability. Such proteins and compositions may be used to aid in the treatment of patients with heart disease, wounds, or other ischemic conditions by stimulating angiogenesis in such patients. These novel forms of VEGF proteins will have a modified affinity for matrix and low affinity receptors. This modification alters the bioavailability of the proteins when administered directly to cells or when cells are transduced with DNA encoding these proteins.

These novel VEGF proteins will possess a unique combination of biological properties that will distinguish them from other VEGF forms. The unique combination of properties of these VEGF proteins will render them preferred therapeutic agents in certain circumstances for the treatment of the cardiovascular system and its diseases as well as other diseases characterized by vascular cell proliferation. In particular, the cDNA coding for these VEGF proteins may be employed in gene therapy for treating the cardiovascular system and its diseases.

The novel VEGF-A proteins comprise amino acid sequences coded for, for example, by VEGF-A exons 1–5, 6b, and 8, or 1–5, 6b, 7, and 8 or a derivative thereof. These proteins preferably do not comprise the full amino acid sequence of exon 6a and, preferably, do not have the same properties, activity, and function of the corresponding VEGF-A proteins that comprise the full amino acid sequence of exon 6a. Other novel VEGF-A proteins comprise amino acid sequences coded for, for example, by VEGF-A exons 1–5, 6a, 6b, and 8. These proteins preferably do not have the same properties, activity, and function of the corresponding VEGF-A proteins that do not comprise exon 6b.

Thus, in preferred embodiments of the invention, a purified polypeptide is provided, comprising an amino acid sequence coded for by VEGF-A exons 1–5, 6b, and 8, or a derivative thereof. In other preferred embodiments of the invention, a purified polypeptide is provided comprising an amino acid sequence coded for by VEGF-A exons 1–5, 6b, 7, and 8, or a derivative thereof.

In other preferred embodiments of the invention, a purified polypeptide is provided comprising an amino acid sequence coded for by VEGF-A exons 1–5, 6a, 6b, and 8, or a derivative thereof. Preferably, the VEGF-A polypeptide of the invention is human VEGF-A. In preferred aspects, the purified polypeptide comprises the amino acid sequence of FIG. 3, FIG. 4, or of FIG. 5.

Also provided in the invention are purified and isolated nucleic acid molecules coding for the purified polypeptides of the invention. Preferably, the nucleic acid molecules have the nucleotide sequence of FIG. 3 or FIG. 4, or of FIG. 5.

Also provided in the present invention are purified and isolated nucleic acid molecules coding for a biologically active fragment of a 6b-modified VEGF protein, preferably VEGF-$A_{138}$, VEGF-$A_{162}$, or VEGF-$A_{182}$, or a derivative thereof. Such fragments maintain most preferably up to 100% of the activity of the full length 6b-modified and have at least 10%, more preferably at least 40%, more preferably at least 80% of the activity of the full length VEGF-$A_{138}$, VEGF-$A_{162}$, or VEGF-$A_{182}$ polypeptides.

Also provided are expression vectors comprising the nucleic acid molecules of the invention. Preferably, these vectors comprise adenovirus sequences; preferably the expression vector is an adenovirus vector. More preferably, the nucleic acid is operably linked to a promoter sequence that is active in vascular endothelial cells. The expression vector preferably further comprises a partial adenoviral sequence from which the E1A/E1B genes have been deleted.

In another embodiment of the invention, a kit is provided for intracoronary injection of a recombinant vector expressing a 6b-modified protein, preferably VEGF-$A_{138}$, VEGF-$A_{162}$, or VEGF-$A_{182}$, comprising: a nucleic acid molecule encoding a 6b-modified protein, preferably VEGF-$A_{138}$, VEGF-$A_{162}$, or VEGF-$A_{182}$, cloned into a vector suitable for expression of said polynucleotide in vivo, a suitable container for said vector, and instructions for injecting said vector into a patient. Preferably, in the kit, the polynucleotide is cloned into an adenovirus expression vector.

In yet another aspect of the invention, a method is provided for treating vascular disease in a mammal comprising the step of administering to said mammal a 6b-modified VEGF-A protein, preferably, VEGF-$A_{138}$, VEGF-$A_{162}$, or VEGF-$A_{182}$, or other 6b-modified VEGF-A protein in a therapeutically effective amount to stimulate vascular cell proliferation.

In another aspect of the invention, a method is provided for enhancing endothelialization of diseased vessels comprising the step of administering to a mammal a therapeutically effective amount of a 6b-modified protein, preferably VEGF-$A_{138}$, VEGF-$A_{162}$, or VEGF-$A_{182}$. Preferably, the endothelialization is reendothelialization after angioplasty. More preferably, the reendothelialization reduces or prevents restenosis.

In further aspects of these methods of the invention, the patient is treated with or without a stent. Preferably, the mammals used in the methods of the invention are human, however, it is contemplated that all mammals would be candidates for these methods. In the methods of the invention, the administration may comprise gene therapy. In preferred methods, the gene for gene therapy is administered using an inflatable balloon catheter coated with a polynucleotide encoding 6b-modified VEGF protein, preferably VEGF-$A_{138}$, VEGF-$A_{162}$, or VEGF-$A_{182}$.

In yet other preferred embodiments of the present invention, the methods, compositions, and vectors of the invention may be used to enhance drug permeation by tumors comprising administering to a patient a 6 b-modified VEGF-A protein or a nucleic acid molecule coding for a 6b-modified VEGF-A protein, preferably VEGF-$A_{138}$, VEGF-$A_{162}$, or VEGF-$A_{182}$. The 6b-modified VEGF-A protein may be delivered directly to a tumor cell, or it may be delivered into the vascular system, preferably at a site located close to the site of the tumor. Thus, delivery of the 6b-modified VEGF-A protein in conjunction with chemotherapy to remove or reduce the size of a tumor, will help to enhance the effectiveness of the chemotherapy by increasing drug uptake by the tumor. The 6b-modified VEGF-A protein delivered in this method may either be through direct delivery of the polypeptide or protein, or through gene therapy.

Thus, provided in the present invention is a method of enhancing drug permeation by tumors comprising administering to a patient a nucleic acid molecule coding for a 6b-modified VEGF-A protein, preferably VEGF-$A_{138}$, VEGF-$A_{162}$, or $VEGF_{182}$. Preferably, the 6b-modified VEGF-A protein is delivered directly into a tumor cell.

In another aspect of the invention, a therapeutic composition is provided comprising a pharmaceutically acceptable carrier and a 6b-modified VEGF protein, preferably VEGF-$A_{138}$, VEGF-$A_{162}$, or $VEGF_{182}$, in a therapeutically effective amount to stimulate vascular cell proliferation. Also provided as an aspect of the invention is a filtered injectable adenovirus vector preparation, comprising: a recombinant adenoviral vector, said vector containing no wild-type virus and comprising: a partial adenoviral sequence from which the E1A/E1B genes have been deleted, and a transgene coding for a 6b-modified VEGF protein, preferably VEGF-$A_{138}$, VEGF-$A_{162}$, or VEGF-$A_{182}$, driven by a promoter flanked by the partial adenoviral sequence; and a pharmaceutically acceptable carrier.

In further embodiments of the invention are provided methods for treating cardiovascular disease in a mammal comprising the step of transfecting cells of said mammal with a nucleic acid molecule which encodes an amino acid sequence coded for by VEGF-A exons 1–5, 6b and 8. Also provided are methods for treating cardiovascular disease in a mammal comprising the step of transfecting cells of said mammal with a nucleic acid molecule which encodes an amino acid sequence coded for by VEGF-A exons 1–5, 6b, 7, and 8. Also provided are methods for treating cardiovascular disease in a mammal comprising the step of transfecting cells of said mammal with a nucleic acid molecule which encodes an amino acid sequence coded for by VEGF-A exons 1–5, 6a, 6b, and 8.

Preferably, the nucleic acid molecule employed in the methods of the invention codes for VEGF-$A_{138}$, VEGF-$A_{162}$, or VEGF-$A_{182}$. In preferred embodiments, the nucleic acid molecule is cloned into a vector. Preferably, the vector comprises adenovirus particles. Preferably, the adenovirus vector particles are delivered to said mammal by injection. Preferably, the number of said adenovirus particles is between about $10^8$ to about $10^{14}$, more preferably between about $10^{10}$ to about $10^{14}$.

In further preferred aspects, the polynucleotide which encodes a 6b-modified VEGF protein, preferably VEGF-$A_{138}$, VEGF-$A_{162}$, or VEGF-$A_{182}$, is delivered to the heart of a mammal. Intracoronary delivery of the polynucleotide is preferred, preferably according to the methods set forth in PCT/US96/02631, published Sep. 6, 1996 as WO96/26742, hereby incorporated by reference herein. Preferably, an intracoronary injection is conducted about 1 cm into the lumens of the left and right coronary arteries.

Thus, in preferred embodiments, the transfected cells are muscle cells, including but not limited to myoblasts, myocytes, cardiomyocytes, cardioblasts, and smooth muscle cells. Preferably, the cells are cardiomyocytes. More preferably, the transfected cells are coronary artery cells and said injection is intracoronary injection. More preferably, the adenovirus particles are injected at about 1 cm into the lumens of the left and right coronary arteries.

Preferably, these methods further comprise administering a potentiating agent that potentiates the angiogenic effect of the 6b-modified VEGF-A polypeptide. Preferably, the potentiating agent is an angiogenic FGF. More preferably, the potentiating agent is selected from the group consisting of FGF-1, FGF-2, FGF-4, FGF-5, and FGF-6.

In one preferred aspect of the methods of the invention, the cells are transfected in vivo. In other preferred aspects, the said cells are transfected ex vivo.

Endothelial cell proliferation, such as that which occurs in angiogenesis, is also useful in preventing restenosis following balloon angioplasty. The balloon angioplasty procedure often injuries the endothelial cells lining the inner walls of blood vessels. Smooth muscle cells often infiltrate into the opened blood vessels causing a secondary obstruction in a process known as restenosis. The proliferation of the endothelial cells located at the periphery of the balloon-induced damaged area in order to cover the luminal surface of the vessel with a new monolayer of endothelial cells would potentially restore the original structure of the blood vessel.

Thus, the present invention provides a method of treating cardiovascular disease in a mammal comprising the step of transfecting cells of said mammal with a polynucleotide which encodes a 6b-modified VEGF-A protein, preferably $VEGF_{138}$, VEGF-$A_{162}$, or VEGF-$A_{182}$. In preferred aspects, the polynucleotide is cloned into a vector. In further preferred aspects, the vector is an adenovirus vector. The adenovirus vector is preferably delivered to the mammal by injection; preferably, about $10^8$ to about $10^{14}$ adenovirus vector particles are delivered in the injection. More preferably, about $10^{11}$ to about $10^{13}$ adenovirus vector particles are delivered in the injection. Most preferably, about $10^{12}$ adenovirus vector particles are delivered in the injection.

Thus in further preferred embodiments, the nucleic acid molecule is introduced into the coronary artery by a catheter inserted into said artery. Preferably, the catheter comprises an inflatable balloon having an outer surface adapted to engage the inner wall of said artery, and wherein said nucleic acid molecule is disposed upon said balloon outer surface.

In preferred aspects of the methods of the invention, the nucleic acid molecule comprises the nucleotide sequence of FIG. 3, FIG. 4, or FIG. 5.

In other aspects of the invention, transformed or transfected host cells are provided which comprise the expression vectors of the invention. Such host cells may be used in, for example, methods of producing a VEGF-A polypeptide comprising growing, under suitable conditions, a host cell transformed or transfected with the recombinant DNA expression vector of the invention in a manner allowing expression of said polypeptide, and isolating said polypeptide from the host cell.

Also provided in the present invention is a method of treating a patient suffering from an ischemic condition comprising administering a therapeutic amount of a pharmaceutical composition comprising a 6b-modified VEGF protein, preferably VEGF-$A_{138}$, VEGF-$A_{162}$, or VEGF-$A_{182}$, in a suitable carrier. Preferably, this method further comprises administering an agent that potentiates the therapeutic effect of said 6b-modified VEGF-A polypeptide. Preferably, the potentiating agent is selected from the group consisting of FGF-1, FGF-2, FGF-4, FGF-5, and FGF-6. Further, said ischemic condition is preferably selected from the group consisting of: cardiac infarction, chronic coronary ischemia, chronic lower limb ischemia, stroke, and peripheral vascular disease.

For the treatment of peripheral conditions, such as peripheral vascular disease, administration of the pharmaceutical compositions of the present invention is preferably by delivery of a modified VEGF-A polypeptide or polynucleotide (or a vector comprising such a polynucleotide) to a peripheral tissue in vivo. Preferably, this is achieved by direct injection into the peripheral tissue, or by introduction into a blood vessel that supplies the peripheral tissue.

Also provided in the present invention are methods of increasing vascular permeability comprising administering a therapeutic amount of a pharmaceutical composition comprising a 6b-modified VEGF-A protein, preferably VEGF-$A_{138}$, VEGF-$A_{162}$, or VEGF-$A_{182}$ in a suitable carrier.

Also provided in the present invention are methods of treating a patient suffering from a wound comprising administering a therapeutic amount of a pharmaceutical composition comprising a 6b-modified VEGF protein preferably VEGF-$A_{138}$ VEGF-$A_{162}$, or VEGF-$A_{182}$ in a suitable carrier.

With the foregoing and other objects, advantages and features of the invention that will become hereinafter apparent, the nature of the invention may be more clearly understood by reference to the following detailed description of the invention, the figures, and the appended claims.

BRIEF DESCRIPTION OF THE DRAWINGS

FIG. 2 depicts the nucleotide [SEQ ID NOS. 9, 11, 13, 15, 17, 19, 21 and 25] and amino acid sequences [SEQ ID NOS. 8, 10, 12, 14, 16, 18, 20 and 22] of VEGF-$_{206}$, with the exons indicated by underline. Nucleotides present in mature VEGF-$A_{206}$ transcripts are shown in uppercase letters. Nucleotides present in the 5' flanking regions and introns are in lower case letters. The alanine residue corresponding to the amino terminus of the mature protein, after the amino terminal secretion signal sequence is cleaved off, is indicated with an asterisk.

FIG. 3 depicts the nucleotide [SEQ ID NO. 25] and amino acid sequences [SEQ ID NO. 24] of the VEGF-$A_{138}$ protein coding region. The alanine residue corresponding to the amino terminus of the mature protein, after the amino terminal secretion signal sequence is cleaved off, is indicated with an asterisk.

FIG. 4 depicts the nucleotide [SEQ ID NO. 27] and amino acid sequences [SEQ ID NO. 26] of the VEGF-$A_{182}$ protein coding region. The alanine residue corresponding to the amino terminus of the mature protein, after the amino terminal secretion signal sequence is cleaved off, is indicated with an asterisk.

FIG. 5 depicts the nucleotide [SEQ ID NO. 29] and amino acid sequences [SEQ ID NO. 28] of the VEGF-$A_{162}$ protein coding region. The alanine residue corresponding to the amino terminus of the mature protein, after the amino terminal secretion signal sequence is cleaved off, is indicated with an asterisk.

DETAILED DESCRIPTION OF THE INVENTION

Figure 1:
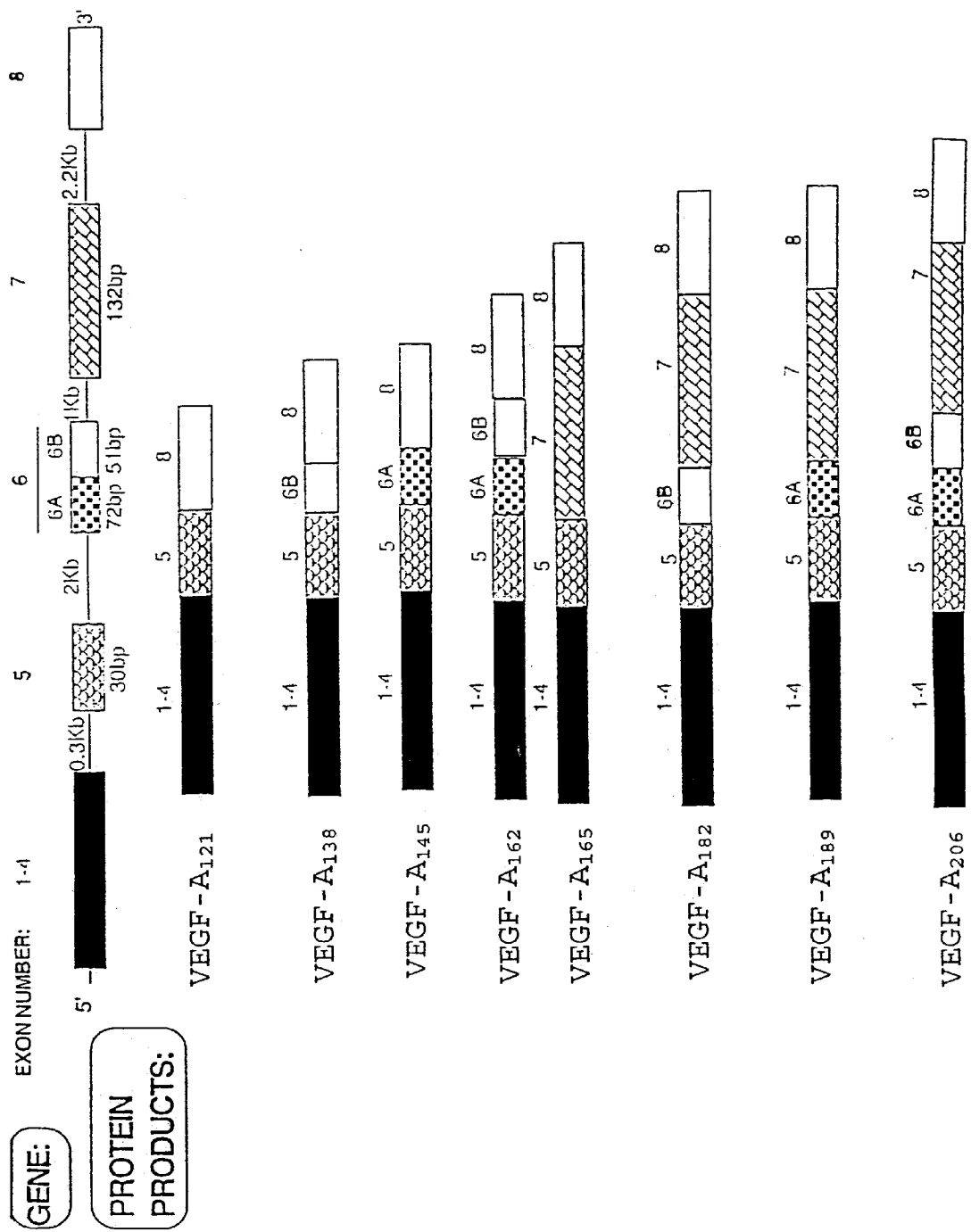
FIG. 1 is a graphic depiction of the exons that encode various VEGF isoforms.

| | |
|---|---|
| BCE | Bovine corneal endothelial cells |
| BFGF | Basic fibroblast growth factor |
| ECM | Extracellular matrix |
| HUVEC | Human umbilical vein derived endothelial cells |
| VEGF | Vascular endothelial growth factor |
| VEGF-A | Vascular endothelial growth factor-A |
| VEGF-$A_{xxx}$ | Vascular endothelial growth factor-A form containing a designated number (xxx) of amino-acids. |
| 6b-modified VEGF-A | Vascular endothelial growth factor protein comprising exon 6b, not including VEGF-$A_{206}$. |

The present invention relates to novel VEGF-A protein products, and nucleic acids encoding the novel protein products comprising, for example, exons 1–5, 6b and 8, 1–5, 6b, 7 and 8, or 1–5, 6a, 6b, and 8, of VEGF-A proteins, and their uses thereof in treating cardiovascular disease. As used herein "cardiovascular disease" means disease which results from a cardiovascular insufficiency, including, but not limited to, coronary artery disease, congestive heart failure, and peripheral vascular disease. The methods of the present invention relate to the treatment of mammalian patients, preferably humans.

"VEGF-$A_{138}$" refers to a form of VEGF-A containing about 138 amino-acids and containing the peptides encoded by exons 1–5, 6b and 8 of the VEGF-A gene. The term "VEGF-$A_{138}$" also refers to derivatives and functional equivalents of the native VEGF-$A_{138}$ nucleic acid or amino acid sequence. Mature VEGF-$A_{138}$ monomers comprise the amino acid sequence shown in FIG. 3. However, as used herein, the term VEGF-$A_{138}$ refers to both the mature form and the pro-form of VEGF-$A_{138}$, including a signal sequence, or derivatives or functional equivalents thereof.

"VEGF-$A_{182}$" refers to a form of VEGF-A containing about 182 amino-acids and containing the peptides encoded by exons 1–5, 6b, 7 and 8 of the VEGF-A gene. The term "VEGF-$A_{182}$" also refers to derivatives and functional equivalents of the native VEGF-$A_{182}$ nucleic acid or amino acid sequence. Mature VEGF-$A_{182}$ monomers comprise the amino acid sequence shown in FIG. 4. However, as used herein, the term VEGF-$A_{182}$ refers to both the mature form and the pro-form of VEGF-$A_{182}$, including a signal sequence, or derivatives or functional equivalents thereof.

"VEGF-$A_{162}$" refers to a form of VEGF-A containing about 162 amino-acids and containing the peptides encoded by exons 1–5, 6a, 6b and 8 of the VEGF-A gene. The term "VEGF-$A_{162}$" also refers to derivatives and functional equivalents of the native VEGF-$A_{162}$ nucleic acid or amino acid sequence. Mature VEGF-$A_{162}$ monomers comprise the amino acid sequence shown in FIG. 5. However, as used herein, the term VEGF-$A_{162}$ refers to both the mature form and the pro-form of VEGF-A$_{162}$, including a signal sequence, or derivatives or functional equivalents thereof.

"Derivatives" of a VEGF-A$_{138}$, VEGF-A$_{162}$, VEGF-A$_{182}$ or other 6b-modified VEGF protein are functional equivalents having similar amino acid sequences and retaining, to some extent, the activities of VEGF-A$_{138}$, VEGF-A$_{162}$, VEGF-A$_{182}$, or other 6b-modified VEGF protein. By "functional equivalent" is meant the derivative has an activity that can be substituted for the activity of VEGF-A$_{138}$, VEGF-A$_{162}$, VEGF-A$_{182}$, or other 6b-modified VEGF protein. Preferred functional equivalents retain the full level of activity of VEGF-A$_{138}$, VEGF-A$_{162}$, VEGF-A$_{182}$ or other 6b-modified VEGF protein as measured by assays known to these skilled in the art, and/or in the assays described herein. Preferred functional equivalents have activities that are within 1% to 10,000% of the activity of VEGF-A$_{138}$, VEGF-A$_{162}$, VEGF-A$_{182}$ or other 6b-modified VEGF protein, more preferably between 10% to 1000%, and more preferably within 50% to 200%. Derivatives have at least 50% sequence similarity, preferably 70%, more preferably 90%, and even more preferably 95% sequence similarity to VEGF-A$_{138}$, VEGF-A$_{162}$, VEGF-A$_{182}$ or similarly 6b-modified VEGF protein. "Sequence similarity" refers to "homology" observed between amino acid sequences in two different polypeptides, irrespective of polypeptide origin.

The ability of the derivative to retain some activity can be measured using techniques described herein and/or using techniques known to those skilled in the art for measuring the activity of other VEGF-A isoforms. Derivatives include modification occurring during or after translation, for example, by phosphorylation, glycosylation, crosslinking, acylation, proteolytic cleavage, linkage to an antibody molecule, membrane molecule or other ligand (see Ferguson et al., 1988, *Annu. Rev. Biochem.* 57:285–320).

Specific types of derivatives also include amino acid alterations such as deletions, substitutions, additions, and amino acid modifications. A "deletion" refers to the absence of one or more amino acid residue(s) in the related polypeptide. An "addition" refers to the presence of one or more amino acid residue(s) in the related polypeptide. Additions and deletions to a polypeptide may be at the amino terminus, the carboxy terminus, and/or internal. Amino acid "modification" refers to the alteration of a naturally occurring amino acid to produce a non-naturally occurring amino acid. A "substitution" refers to the replacement of one or more amino acid residue(s) by another amino acid residue(s) in the polypeptide. Derivatives can contain different combinations of alterations including more than one alteration and different types of alterations.

Although the effect of an amino acid change varies depending upon factors such as phosphorylation, glycosylation, intra-chain linkages, tertiary structure, and the role of the amino acid in the active site or a possible allosteric site, it is generally preferred that the substituted amino acid is from the same group as the amino acid being replaced. To some extent the following groups contain amino acids which are interchangeable: the basic amino acids lysine arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be inter- changeable to some extent, and cysteine additionally fits into this group, or may be classified with the polar neutral amino acids.

Although proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp).

Examples of modified amino acids include the following: altered neutral nonpolar amino acids such as amino acids of the formula $H_2N(CH_2)_nCOOH$ where n is 2–6, sarcosine (Sar), t-butylalanine (t-BuAla), t-butylglycine (t-BuGly), N-methyl isoleucine (N-MeIle), and norleucine (Nleu); altered neutral aromatic amino acids such as phenylglycine; altered polar, but neutral amino acids such as citrulline (Cit) and methionine sulfoxide (MSO); altered neutral and nonpolar amino acids such as cyclohexyl alanine (Cha), altered acidic amino acids such as cysteic acid (Cya); and altered basic amino acids such as ornithine (Orn).

Preferred derivatives have one or more amino acid alteration(s) that do not significantly affect the receptor-binding or other activity of the 6b-modified VEGF protein. In regions of the 6b-modified VEGF polypeptide sequence not necessary for the 6b-modified VEGF protein activity, amino acids may be deleted, added or substituted with less risk of affecting activity. In regions required for the 6b-modified VEGF protein activity, amino acid alterations are less preferred as there is a greater risk of affecting activity. Such alterations should be conservative alterations. For example, one or more amino acid residues within the sequence can be substituted by another amino acid of a similar polarity which acts as a functional equivalent.

Conserved regions tend to be more important for protein activity than non-conserved regions. Standard procedures can be used to determine the conserved and non-conserved regions important for receptor activity using in vitro mutagenesis techniques or deletion analyses and measuring receptor activity as described by the present disclosure.

Derivatives can be produced using standard chemical techniques and recombinant nucleic acid molecule techniques. Modifications to a specific polypeptide may be deliberate, as through site-directed mutagenesis and amino acid substitution during solid-phase synthesis, or may be accidental such as through mutations in hosts which produce the polypeptide. Polypeptides including derivatives can be obtained using standard techniques such as those described in Sambrook et al., *Molecular Cloning*, Cold Spring Harbor Laboratory Press (1989). For example, Chapter 15 of Sambrook describes procedures for site-directed mutagenesis of cloned DNA.

In one aspect the invention features a nucleic acid molecule, or polynucleotide encoding a 6b-modified VEGF protein. In some situations it is desirable for such nucleic acid molecule to be isolated or enriched, or purified. By the use of the term "enriched" in reference to nucleic acid molecule, polypeptide, or protein is meant that the specific DNA or RNA sequence, polypeptide, or protein constitutes a significantly higher fraction (2–5 fold) of the total DNA, RNA, polypeptide or protein present in the cells or solution of interest than in normal or diseased cells or in the cells from which the sequence was taken. This could be caused, for example, by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUCI9. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

Use of the term "isolated" indicates that a DNA, RNA or protein has been removed from its naturally occurring environment. Thus, the sequence may be in a cell-free solution or placed in a different cellular environment. The term does not imply that the sequence is the only nucleotide chain or polypeptide present, but that it is essentially free (about 90–95% pure at least) of non-nucleotide or non-peptide material naturally associated with it.

It is also advantageous for some purposes that a nucleotide sequence or polypeptide be in purified form, e.g., cloned or recombinant. The term "purified" does not require absolute purity (such as a homogeneous preparation); instead, it represents an indication that the sequence is relatively purer than in the natural environment (compared to the natural level this level should be at least 2–5 fold greater, e.g., in terms of mg/ml).

The nucleic acid molecule may be constructed, for example, from an existing VEGF-A nucleotide sequence by modification using, for example, oligonucleotide site-directed mutagenesis, by deleting sequences using restriction enzymes, by adding sequences obtained by subcloning or PCR, or as described herein. Standard recombinant techniques for mutagenesis such as in vitro site-directed mutagenesis (Hutchinson et al., *J. Biol. Chem.* 253:6551, (1978), Sambrook et al., Chapter 15, supra), use of TAB® linkers (Pharmacia), and PCR-directed mutagenesis can be used to create such mutations. The nucleic acid molecule may also be synthesized by the triester method or by using an automated DNA synthesizer.

The invention also features recombinant DNA vectors, preferably in a cell or an organism. The recombinant DNA vectors may contain a sequence coding for a VEGF-$A_{138}$, VEGF-$A_{162}$, VEGF-$A_{182}$. or other 6b-modified VEGF-A protein or a functional derivative thereof in a vector containing a promoter effective to initiate transcription in a host cell. The recombinant DNA vector may contain a transcriptional initiation region functional in a cell and a transcriptional termination region functional in a cell. Where the DNA vector contains sufficient control sequences, such as initiation and/or termination regions, such that the inserted nucleic acid molecule may be expressed in a host cell, the vector may also be called an "expression vector."

The present invention also relates to a cell or organism that contains the above-described nucleic acid molecule or recombinant DNA vector and thereby is capable of expressing a VEGF-$A_{138}$, VEGF-$A_{162}$, VEGF-$A_{182}$, or other 6b-modified VEGF-A peptide. The peptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

For example, the entire coding sequence of VEGF-$A_{138}$ may be combined with one or more of the following in an appropriate expression vector to allow for such expression: (1) an exogenous promoter sequence (2) a ribosome binding site (3) a polyadenylation signal (4) a secretion signal (5) a promiscuous or tissue specific enhancer. Modifications can be made in the 5'-untranslated and 3'-untranslated sequences to improve expression in a prokaryotic or eukaryotic cell, or codons may be modified such that while they encode an identical amino acid, that codon may be a preferred codon in the chosen expression system. The use of such preferred codons is described in, for example, Grantham et al., *Nuc. Acids Res.*, 9:43–74 (1981), and Lathe, *J. Mol. Biol.* 183:1–12 (1985) hereby incorporated by reference herein in their entirety. These publications, and all other publications referenced herein, are hereby incorporated by reference in their entirety.

If desired, the non-coding region 3' to the genomic VEGF-A protein sequence may be operably linked to the nucleic acid molecule encoding, for example, VEGF-$A_{138}$. This region may be used in the recombinant DNA vector for its transcriptional termination regulatory sequences, such as termination and polyadenylation. Thus, by retaining the 3' region naturally contiguous to the DNA sequence encoding VEGF-A transcriptional termination signals, or sequences involved in message stability may be provided. Alternatively, a 3' region functional in the host cell may be substituted.

An operable linkage is a linkage in which the regulation, DNA sequences and the DNA sequence sought to be expressed are connected in such a way as to permit gene sequence expression. Two DNA sequences (such as a promoter region sequence and a VEGF-$A_{138}$ protein sequence) are said to be operably linked if the nature of the linkage between the two DNA sequences does not (1) result in the introduction of a frame-shift mutation in the coding sequence, (2) interfere with the ability of the promoter region sequence to direct the transcription of VEGF-$A_{138}$ protein gene sequence, or (3) interfere with the ability of the VEGF-$A_{138}$ protein gene sequence to be transcribed by the promoter region sequence. Thus, a promoter region would be operably linked to a DNA sequence if the promoter were capable of effecting transcription of that DNA sequence. Thus, to express a VEGF-$A_{138}$, transcriptional and translational signals recognized by an appropriate host are necessary.

Those skilled in the art will recognize that the novel VEGF proteins of the present invention may also be expressed in various cell systems, both prokaryotic and eukaryotic, all of which are within the scope of the present invention.

Although the novel VEGF proteins of the present invention may be expressed in prokaryotic cells, which are generally very efficient and convenient for the production of recombinant proteins, the VEGF proteins produced by such cells will not be glycosylated and therefore may have a shorter half-life in vivo. Prokaryotes most frequently are represented by various strains of *E. coli*. However, other microbial strains may also be used, including other bacterial strains. Recognized prokaryotic hosts include bacteria such as *E. coli*, Bacillus, Streptomyces, Pseudomonas, Salmonella, Serratia, and the like. The prokaryotic host must be compatible with the replicon and control sequences in the expression plasmid.

In prokaryotic systems, plasmid vectors that contain replication sites and control sequences derived from a species compatible with the host may be used. Examples of suitable plasmid vectors may include pBR322, PUC118, pUC119 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

To express VEGF pplypeptides or subunits (or a functional derivative thereof) in a prokaryotic cell, it is necessary to operably link the 6b-modified VEGF nucleic acid sequence to a functional prokaryotic promoter. Such promoters may be either constitutive or, more preferably, regulatable (i.e., inducible or repressible). Examples of constitutive promoters include the int promoter of bacteriophage λ., the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176–182 (1985)) and the __-28-specific promoters of *B. subtilis* (Gilman et at., *Gene sequence* 32:11–20(1984)), the promoters of the bacteriophages of Bacillus (Gryczan, In: *The Molecular Biology of the Bacilli*, Academic Press, Inc., NY (I 982)), and Streptomyces promoters (Ward et at., *Mol. Gen. Genet.* 203:468–478(1986)). Prokaryotic promoters are reviewed by Glick (*J. Ind. Microbiot.* 1:277–282(1987)); Cenatiempo (*Biochimie* 68:505–516(1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding. sites are disclosed, for example, by Gold et at. (*Ann. Rev. Microbiol.* 35:365–404(1981)). The tibosome binding site and other sequences required for translation initiation are operably linked to the nucleic acid molecule coding for VEGF-$A_{145}$ by, for example, in frame ligation of synthetic oligonucleotides that contain such control sequences. For expression in prokaryotic cells, no signal peptide sequence is required. The selection of control sequences, expression vectors, transformation methods, and the like, are dependent on the type of host cell used to express the gene.

As used herein, "cell", "cell line", and "cell culture" may be used interchangeably and all such designations include progeny. Thus, the words "transformants" or "transformed cells" include the primary subject cell and cultures derived therefrom, without regard to the number of transfers. For example, VEGF-$A_{138}$ expressed in prokaryotic cells is expected to comprise a mixture of properly initiated VEGF-$A_{138}$ protein peptides with the N-terminal sequence predicted from the sequence of the expression vector, and VEGF-$A_{138}$ protein peptides that have an N-terminal methionine resulting from inefficient cleaving of the initiation methionine during bacterial expression. Both types of VEGF-$A_{138}$ peptides are considered to be within the scope of the present invention as the presence of an N-terminal methionine is not expected to affect biological activity. It is also understood that all progeny may not be precisely identical in DNA content, due to deliberate or inadvertent mutations. However, as defined, mutant progeny have the same functionality as that of the originally transformed cell.

Preferred prokaryotic vectors include plasmids such as those capable of replication in *E. coli* (such as, for example, pBR322, ColEl, pSC1O1, pACYC 184, πVX. Such plasmids are, for example, disclosed by Sambrook (cf. "*Molecular Cloning: A Laboratory Manual*", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: *The Molecular Biology of the Bacilli*, Academic Press, NY (1982), pp. 307–329). Suitable Streptomyces plasmids include plJ1O1 (Kendall et al., *J. Bacteriol.* 169:4177–4183 (1987)), and streptomyces bacteriophages such as ϕC31 (Chater et al., In: *Sixth International Symposium on Actinomycetales Biology*, Akademiai Kaido, Budapest, Hungary (1986), pp. 4554). Pseudomonas plasmids are reviewed by John et al. (*Rev. Infect. Dis.* 8:693–704 (1986)), and Izaki (*Jpn. J. Bacteriol.* 33:729–742(1978)).

Eukaryotic host cells that may be used in the expression systems of the present invention are not strictly limited, provided that they are suitable for use in the expression of the 6b-modified VEGF proteins of the invention. Preferred eukaryotic hosts include, for example, yeast, fungi, insect cells, mammalian cells either in vivo, or in tissue culture. Mammalian cells which may be useful as hosts include HeLa cells, cells of fibroblast origin such as Vero or CHO-K1, or cells of lymphoid origin and their derivatives.

The 6b-modified VEGF proteins of the present invention may also be expressed in human cells such as human embryo kidney 293EBNA cells, which express Epstein-Barr virus nuclear antigen 1, as described, for example, in Olofsson, B. et al., *Proc. Natl. Acad. Sci. USA* 93:2576–2581 (1996). The cells are transfected with the expression vectors by using, for example, a calcium phosphate precipitation or lipofection method, and the cells are then incubated-for at least 48 hours. The VEGF peptides may then be purified from the supernatant as described in Example II.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459(1988).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., prepeptides). For a mammalian host, several possible vector systems are available for the expression of the 6b-modified VEGF peptides and of the invention.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of the 6b-modified VEGF protein of the invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310(1981)); the yeast gal4 gene sequence promoter (Johnston et al., *Proc. Natl. Acad. Sci.* (USA) 79:6971–6975(1982); Silver et al., *Proc. Natl. Acad. Sci.* (USA) 81:5951–5955 (1984)).

Translation of eukaryotic MRNA is initiated at the codon which encodes the first methionine. For this reason, it is preferable to ensure that the linkage between a eukaryotic promoter and a DNA sequence that encodes a VEGF-$A_{138}$, VEGF-$A_{162}$, VEGF-$A_{182}$, or other 6b-modified VEGF protein, a functional derivative thereof, does not contain any intervening codons which are capable of encoding a methionine (i.e., AUG). The presence of such codons results either in a formation of a fusion protein (if the AUG codon is in the same reading frame as, for example, the VEGF-$A_{138}$ protein coding sequence) or a frame-shift mutation (if the AUG codon is not in the same reading frame as, for example, the VEGF-$A_{138}$ protein coding sequence).

A 6b-modified VEGF nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Because such molecules are incapable of autonomous replication, the expression of the gene may occur through the transient expression of the introduced sequence. Alternatively, permanent expression may occur through the integration of the introduced DNA sequence into the host chromosome.

A vector may be employed that is capable of integrating the desired gene sequences into the host cell chromosome. Cells that have stably integrated the introduced DNA into their chromosomes can be selected by also introducing one or more markers that allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host and whether it is desirable to be able to "shuttle" the vector between host cells of different species.

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274(1982); Broach, In: *"The Molecular Biology of the Yeast Saccharomyces: Life Cycle and Inheritance",* Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise,* Vol. 3, Gene Sequence Expression, Academic Press, NY, pp. 563–608(1980).

A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ('Ad'), adeno-associated viruses (AAV), and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available (see, e.g., the various references cited herein).

In preferred methods of enhancing cardiac function according to one of the preceding embodiments, the vector is a viral vector or a lipid-based vector, preferably a viral vector. The vector can be a targeted vector, especially a targeted vector that preferentially binds to ventricular myocytes. Presently preferred viral vectors are derived from adenovirus (Ad) or adeno-associated virus (AAV). Both human and non-human viral vectors can be used but preferably the recombinant viral vector is replication-defective in humans. Where the vector is an adenovirus, it preferably comprises a polynucleotide having a promoter operably linked to a gene encoding an angiogenic protein or peptide, and is replication-defective in humans.

Presently preferred replication-defective adenoviral vectors have deletions that remove the E1A and E1B genes, or have deletions that remove the E1A, E1B and E4 genes. Preferably about $10^{10}$ to $10^{14}$ adenovirus vector particles, more preferably about $10^{11}$ to $10^{13}$ vector particles, most preferably about $10^{12}$ vector particles, are introduced into a blood vessel, preferably a blood vessel supplying the myocardium.

For AAV vectors, the vector preferably comprises a polynucleotide having a promoter operably linked to a gene encoding an angiogenic protein or peptide, and preferably, the gene encoding the angiogenic protein or peptide is flanked by AAV inverted terminal repeats (ITRs). Preferably, the AAV vector is replication-defective in humans. Presently preferred replication-defective AAV vectors have deletions affecting one or more AAV replication or encapsidation sequences. Alternatively, the vector can be a lipid-based vector comprising a gene encoding an angiogenic protein or peptide as described herein.

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, lipofection, calcium phosphate precipitation, direct microinjection, DEAE-dextran transfection, and the like. The most effective method for transfection of eukaryotic cell lines with plasmid DNA varies with the given cell type. After the introduction of the vector, recipient cells are grown in a selective medium, which selects for the growth of vector-containing cells. Expression of the cloned gene molecule(s) results in the production of a 6b-modified VEGF. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

Production of the stable transfectants, may be accomplished by, for example, by transfection of an appropriate cell line with a eukaryotic expression vector, such as pCEP4, in which the coding sequence for the 6b-modified VEGF protein has been cloned into the multiple cloning site. These expression vectors contain a promoter region, such as the human cytomegalovirus promoter (CMV), that drive high-level transcription of desired DNA molecules in a variety of mammalian cells. In addition, these vectors contain genes for the selection of cells that stably express the DNA molecule of interest. The selectable marker in the pCEP4 vector encodes an enzyme that confers resistance to hygromycin, a metabolic inhibitor that is added to the culture to kill the nontransfected. cells.

Cells that have stably incorporated the transfected DNA may be identified by their resistance to selection media, as described above, and clonal cell lines will be produced by expansion of resistant colonies. The expression of a 6b-modified VEGF protein by these cell lines may be assessed by methods known in the art, for example, by RNAse protection assay, Northern blot, or Western blot analysis.

Pharmaceutical Compositions and Therapeutic Uses

One object of this invention is to provide VEGF-$A_{138}$, VEGF-$A_{162}$, VEGF-$A_{182}$, or other 6b-modified VEGF protein in a pharmaceutical composition suitable for therapeutic use. Thus, in one aspect the invention provides a method for stimulating vascular cell proliferation in a patient by administering a therapeutically effective amount of pharmaceutical composition comprising VEGF-$A_{138}$, VEGF-$A_{162}$, VEGF-$A_{182}$. or other 6b-modified VEGF protein.

By "therapeutically effective amount" is meant an amount of a compound that produces the desired therapeutic effect in a patient. For example, in reference to a disease or disorder, it is the amount which reduces to some extent one or more symptoms of the disease or disorder, and returns to normal, either partially or completely, physiological or biochemical parameters associated or causative of the disease or disorder. When used to therapeutically treat a patient it is an amount expected to be between 0.1 mg/kg of protein to 100 mg/kg, preferably less than 50 mg/kg, more preferably less than 10 mg/kg, more preferably less than 1 mg/kg. The amount of compound depends on the age, size, and disease associated with the patient and can be determined by standard procedure. Thus, for gene therapy, a therapeutically effective amount would be an amount sufficient to direct the expression and secretion of such an amount of protein in a patient.

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other mammals such as other primates, farm animals such as swine, cattle and poultry, and sports animals and pets such as horses, dogs and cats.

Preferably, the therapeutically effective amount is provided as a pharmaceutical composition. A pharmacological agent or composition refers to an agent or composition in a form suitable for administration into a multicellular organism such as a human. Suitable forms, in part, depend upon the use or the route of entry, for example oral, transdermal, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms which prevent the agent or composition from exerting its effect.

The claimed compositions can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cyclohexylsulfonate, cyclohexylsulfamate and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclcohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent Such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

The desired isotonicity may be accomplished using sodium chloride or other pharmaceutically acceptable agents such as dextrose, boric acid, sodium tartrate, propylene glycol, polyols (such as mannitol and sorbitol), or the inorganic or organic solutes. Sodium chloride is preferred particularly for buffers containing sodium ions.

The compounds of the invention can be formulated for a variety of modes of administration, including systemic and topical or localized administration. Techniques and formulations generally may be found in *Remington's Pharmaceutical Sciences,* 18th Edition, Mack Publishing Co., Easton, Pa., 1990. See, also, Wang, Y. J. and Hanson, M. A. "Parenteral Formulations of Proteins and Peptides: Stability and Stabilizers ", *Journal of Parenteral Science and Technology,* Technical Report No. 10, Supp. 42:2S (I 988). A suitable administration format may best be determined by a medical practitioner for each patient individually.

For systemic administration, injection is preferred, e.g., intraperitbneal, subcutaneous, intrathecal, or intracerebroventricular. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, Goodman acetate/acetic acid buffers. A form of repository or "depot" slow release preparation may be used so that therapeutically effective amounts of the preparation are delivered into the bloodstream over many hours or days following transdermal injection or delivery. In addition, the compounds may be formulated in solid form and redissolved or suspended immediately prior to use. Lyophilized forms are also included. An inflatable balloon catheter with VEGF-$A_{145}$ protein coating the balloon may also be employed to deliver the substance to a targeted artery.

Alternatively, the compounds may be administered orally. For oral administration, the compounds are formulated into conventional oral dosage forms such as capsules, tablets and tonics.

Systemic administration can also be by transmucosal or transdermal means, or the molecules can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be, for example, through nasal sprays or using suppositories. For oral administration, the molecules are formulated into conventional oral administration dosage forms such as capsules, tablets, and liquid preparations.

For topical administration, the compounds of the invention are formulated into ointments, salves, gels, or creams, as is generally known in the art.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

The amounts of various compounds of this invention to be administered can be determined by standard procedures.

For use by the physician, the compositions will be provided in dosage unit form containing an amount of VEGF-$A_{138}$, VEGF-$A_{162}$, VEGF-$A_{182}$, or other 6b-modified VEGF protein.

Gene Therapy

Nucleic acids coding for VEGF-$A_{138}$, VEGF-$A_{162}$, VEGF-$A_{182}$, or other 6b-modified VEGF proteins will also be useful in gene therapy (reviewed in Miller, *Nature* 357:455–460 (1992)). Miller states that advances have resulted in practical approaches to human gene therapy that have demonstrated positive initial results. The basic science of gene therapy is described in Mulligan, *Science* 260:926–931 (1993). One example of gene therapy is presented in Example IV, which describes the use of adenovirus-mediated gene therapy.

As another example, an expression vector containing the VEGF-$A_{138}$, VEGF-$A_{162}$, VEGF-$A_{182}$, or other 6b-modified VEGF protein coding sequence may be inserted into cells, the cells are grown in vitro and then infused in large numbers into patients. In another example, a DNA segment containing a promoter of choice (for example a strong promoter) is transferred into cells containing an endogenous VEGF-$A_{138}$, VEGF-$A_{162}$, VEGF-$A_{182}$, or other 6b-modified VEGF protein, should such endogenous forms exist, in such a manner that the promoter segment enhances expression of the endogenous VEGF gene (for example, the promoter segment is transferred to the cell such that it becomes directly linked to the endogenous VEGF gene.

The gene therapy may involve the use of an adenovirus or other vector including a nucleotide sequence coding for VEGF-$A_{138}$, VEGF-$A_{162}$, VEGF-$A_{182}$, or other 6b-modified VEGF protein, or a naked nucleic acid molecule coding for these proteins. Alternatively, engineered cells containing a nucleic acid molecule coding for these modified proteins may be injected. Example IV illustrates the method of gene therapy using an adenovirus vector to provide angiogenesis therapy.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant VEGF-$A_{138}$, VEGF-$A_{162}$, VEGF-$A_{182}$, or other 6b-modified VEGF protein into the targeted cell population. Methods which are well known to those skilled in the art can be used to construct recombinant viral vectors containing coding sequences. See, for example, Nabel, E. G., *Circulation,* 91, 541–548 (1995), the techniques described in Maniatis et al., *Molecular Cloning: A Laboratory Manual,* Cold Spring Harbor Laboratory, N.Y. (1989), and in Ausubel et al., *Current Protocols in Molecular Biology,* Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:397–8, 1989). Several other methods for the direct transfer of plasmid DNA into cells exist for use in human gene therapy and involve targeting the DNA to receptors on cells by complexing the plasmid DNA to proteins. See, Miller, *Nature* 357:455–60, 1992.

In its simplest form, gene transfer can be performed by simply injecting minute amounts of DNA into the nucleus of a cell, through a process of microinjection. Capecchi, M. R., *Cell* 22:479–88 (1980). Once recombinant genes are introduced into a cell, they can be recognized by the cells' normal mechanisms for transcription and translation, and a gene product will be expressed. Other methods have also been attempted for introducing DNA into larger. numbers of cells. These methods include: transfection, wherein DNA is precipitated with $CaPO_4$ and taken into cells by pinocytosis (Chen, C. and Okayama, H., *Mol. Cell Biol.* 7:2745–52 (1987)); electroporation, wherein cells are exposed to large voltage pulses to introduce holes into the membrane (Chu, G. et al., *Nucleic Acids Res.,* 15:1311–26 (1987)); lipofection/liposome fusion, wherein DNA is packaged into lipophilic vesicles which fuse with a target cell (Felgner, P. L., et al., *Proc. Natl. Acad. Sci.* USA. 84:7413–7 (1987)); and particle bombardment using DNA bound to small projectiles (Yang, N. S., et al., *Proc. Natl. Acid Sci..* 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel, D. T., et al., *Am. J. Respir. Cell. Mol. Biol.* 6:247–52 (1992).

A balloon catheter, such as those used in angioplasty may be employed wherein the balloon is coated with VEGF-$A_{138}$, VEGF-$A_{162}$, VEGF-$A_{182}$, or other 6b-modified protein, DNA coding for such protein, or vectors as described in Riessen, R., *Human Gene Therapy,* 4, 749–758 (1993) incorporated herein by reference.

As used herein "gene transfer" means the process of introducing a foreign nucleic acid molecule into a cell. Gene transfer is commonly performed to enable the expression of a particular product encoded by the gene. The product may include a protein, polypeptide, antisense DNA or RNA, or enzymatically active RNA. Gene transfer can be performed in cultured cells or by direct administration into animals. Generally gene transfer involves the process of nucleic acid molecule contact with a target cell by non-specific or receptor mediated interactions, uptake of nucleic acid molecule into the cell through the membrane or by endocytosis, and release of nucleic acid molecule into the cytoplasm from the plasma membrane or endosome. Expression may require, in addition, movement of the nucleic acid molecule into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid molecule or nucleic acid-protein complex into the patient.

In another preferred embodiment, a vector having nucleic acid molecule sequences encoding VEGF-$A_{138}$, VEGF-$A_{162}$, VEGF-$A_{182}$, or other 6b-modified VEGF protein is provided in which the nucleic acid molecule sequence is expressed only in a specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid molecule sequence which is capable of being expressed in vivo in an animal and thereby providing or augmenting the function of an endogenous gene which is missing or defective in the animal.

Vectors for Gene Delivery In Vivo

In general, the gene of interest is transferred to the target organ, preferably the heart, including cardiac myocytes, or skeletal muscle, including skeletal myocytes in vivo and directs production of the encoded protein. Such production may be relatively constitutive. A variety of different gene transfer vectors, including viral as well as non-viral systems, can be employed to deliver transgenes for use in the present invention.

Preferred vectors for use in the present invention include viral vectors, lipid-based vectors and other vectors that are capable of delivering DNA to non-dividing cells in vivo.

Presently preferred are viral vectors, particularly replication-defective viral vectors (including, for example replication-defective adenovirus vectors and adeno-associated virus (AAV) vectors. For ease of production and use in the present invention, replication-defective adenovirus vectors are presently most preferred.

References describing a variety of other gene delivery vectors are known in the art, some of which are cited herein. Such other vectors include, for example, other viral vectors (such as adeno-associated viruses (AAV), liposomes and other lipid-containing complexes, and other macromolecular complexes capable of mediating delivery of a polynucleotide to a host cell. As described above and in the cited references, vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e. positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available (see, e.g., the various references cited above).

Additional references describing adenovirus vectors and other viral vectors which could be used in the methods of the present invention include the following: Horwitz, M. S., Adenoviridae and Their Replication, in Fields, B., et al.. (eds.) Virology, Vol. 2, Raven Press New York, pp. 1679–1721, 1990); Graham, F., et al., pp. 109128 in Methods in Molecular Biology, Vol. 7: Gene Transfer and Expression Protocols, Murray, E. (ed.), Humana Press, Clifton, N.J. (1991); Miller, N., et al., FASEB Journal 9: 190–199, 1995; Schreier, H, Pharmaceutica Acta Helvetiae 68: 145–159, 1994; Schneider and French, Circulation 88:1937–1942, 1993; Curiel D. T., et al., Human Gene Therapy 3: 147–154, 1992; Graham, F. L., et al., WO 95/00655 (Jan. 5, 1995); Falck-Pedersen, E. S., WO 95/16772 (Jun. 22, 1995); Denefle, P. et al., WO 95/23867 (Sep. 8, 1995); Haddada, H. et al., WO 94/26914 (Nov. 24, 1994); Perricaudet, M. et al., WO 95/02697 (Jan. 26, 1995); Zhang, W., et al., WO 95/25071 (Oct. 12, 1995). A variety of adenovirus plasmids are also available from commercial sources, including, e.g., Microbix Biosystems of Toronto, Ontario (see, e.g., Microbix Product Information Sheet: Plasmids for Adenovirus Vector Construction, 1996).

Additional references describing AAV vectors which could be used in the methods of the present invention include the following: Carter, B., Handbook of Parvoviruses, vol. 1, pp. 169–228, 1990; Berns, Virology, pp. 1743–1764 (Raven Press 1990); Carter, B., Curr. Opin. Biotechnol., 3: 533–539, 1992; Muzyczka, N., Current Topics in Microbiology and Immunology, 158: 92–129, 1992; Flotte, T. R., et al., Am. J. Respir. Cell Mol. Biol. 7:349–356, 1992; Chatterjee et al., Ann. NY Acad. Sci., 770: 79–90, 1995; Flotte, T. R., et al., WO 95/13365 (May 18, 1995); Trempe, J. P., et al., WO 95/13392 (May 18, 1995); Kotin, R., Human Gene Therapy, 5: 793–801, 1994; Flotte, T. R., et al., Gene Therapy 2:357–362, 1995; Allen, J. M., WO 96/17947 (Jun. 13, 1996); and Du et al., Gene Therapy 3: 254261, 1996.

Additional references describing non-viral vectors which could be used in the methods of the present invention include the following: Ledley, F D, Human Gene Therapy 6: 11 29–1144, 1995; Miller, N., et al., FASEB Journal 9: 190–199, 1995; Chonn, A., et al., Curr. Opin. in Biotech. 6: 698–708, 1995; Schofield, J P, et al., British Med. Bull. 51: 56–71, –1995; Brigham, K. L., et al., J. Liposome Res. 3: 31 49, 1993; Brigham, K. L., WO 91/06309 (May 16, 1991); Felgner, P. L., et al., WO 91/17424 (Nov. 14, 1991); Solodin et al., Biochemistry 34: 13537–13544, 1995; WO 93/19768 (Oct. 14, 1993); Debs et al., WO 93125673; Felgner, P. L., et al., U.S. Pat. No. 5,264,618 (Nov. 23, 1993); Epand, R. M., et al., U.S. Pat. No. 5,283,185 (Feb. 1, 1994); Gebeyehu et al., U.S. Pat. No. 5,334,761 (Aug. 2, 1994); Felgner, P. L., et al., U.S. Pat. No. 5,459,127 (Oct. 17, 1995); Overell, R. W., et al., WO 95/28494 (Oct. 26, 1995); Jessee, WO 95/02698 (Jan. 26, 1995); Haces and Ciccarone, WO 95/17373 (Jun. 29, 1995); Lin et al., WO 96/01840 (Jan. 25, 1996).

Helper Independent Replication Deficient Human Adenovirus 5 System

In general, the gene of interest is transferred to the heart (or skeletal muscle), including cardiac myocytes (and skeletal myocytes), in vivo and directs constitutive production of the encoded protein. Several different gene transfer approaches are feasible. Preferred is the helper-independent replication deficient human adenovirus 5 system. Using this system, Giordano and Hammond have demonstrated transfection of greater than 60% of myocardial cells in vivo by a single intracoronary injection (Giordano and Hammond, Clin. Res., 42:123A, 1994). Non-replicative recombinant adenoviral vectors are particularly useful in transfecting coronary endothelium and cardiac myocytes resulting in highly efficient transfection after intracoronary injection. The same will be true for transfecting desired cells of the peripheral vascular system.

The helper-independent replication-defective human adenovirus 5 system can be used effectively to transfect a large percentage of myocardial cells in vivo by a single intracoronary injection. Hammond, et al. have also shown that such a delivery technique can be used to effectively target vectors to the myocardium of a large mammal heart. Additional means of targeting vectors to particular cells or tissue types are described below and in the art.

In various illustrations described below, recombinant adenovirus vectors are based on the human adenovirus 5 (as described by McGrory W J, et al., Virology 163:614–617, 1988) which are missing essential early genes from the adenovirus genome (usually E1A/E1B), and are therefore unable to replicate unless grown in permissive cell lines that provide the missing gene products in trans. In place of the missing adenovirus genomic sequences, a transgene of interest can be cloned and expressed in tissue/cells infected with the replication-defective adenovirus. Although adenovirus-based gene transfer does not generally result in stable integration of the transgene into the host genome (less than 0.1% adenovirus-mediated transfections result in transgene incorporation into host DNA), adenovirus vectors can be propagated in high titer and transfect non-replicating cells; and, although the transgene is not passed to daughter cells, this is suitable for gene transfer to adult cardiac myocytes, which do not actively divide. Retrovirus vectors provide stable gene transfer, and high titers are now obtainable via retrovirus pseudotyping (Burns, et al., Proc Nat'l Acad Sci (USA) 90: 8033–8037, 1993), but current retrovirus vectors are generally unable to efficiently transduce nonreplicating cells.

An advantage associated with nondividing cells such as myocytes is that the viral vector is not readily "diluted out" by host cell division. To further enhance the duration of transgene expression in the heart, however, it is also possible to employ various second generation adenovirus vectors that have both E1 and E4 deletions, which can be used in conjunction with cyclophosphamide administration (See, e.g., Dai et al., Proc. Nat'l Acad Sci. (USA) 92: 1401–1405, 1995). To further increase the extent of initial gene transfer, multiple infusions, or infusion in an isolated coronary circuit can also be employed.

Human 293 cells, which are human embryonic kidney cells transformed with adenovirus E1A/E1B genes, typify useful permissive cell lines for the production of such replication-defective vectors. However, other cell lines which allow replication-defective adenovirus vectors to propagate therein can also be used, such as HeLa cells.

The recombinant adenoviral vectors based on the human adenovirus 5 (Virology, 163:614–617, 1988) are missing essential early genes from the adenoviral genome (usually E1A/E1B), and are therefore unable to replicate unless grown in permissive cell lines that provide the missing gene products in trans. In place of the missing adenoviral genomic sequences, a transgene of interest can be cloned and expressed in tissue/cells infected with the replication deficient adenovirus. Although adenovirus-based gene transfer does not result in integration of the transgene into the host genome (less than 0.1% adenovirus-mediated transfections result in transgene incorporation into host DNA), and therefore is not stable, adenoviral vectors can be propagated in high titer and transfect non-replicating cells. Although the transgene is not passed to daughter cells, this is acceptable for gene transfer to adult skeletal muscle and cardiac myocytes, which do not divide. Retroviral vectors provide stable gene transfer, and high titers are now obtainable via retrovirus pseudotyping (Burns, et al., Proc. Natl. Acad. Sci. (USA), 90:8033–8037, 1993), but current retroviral vectors are unable to transduce nonreplicating cells (adult skeletal muscle and cardiac myocytes) efficiently. In addition, the potential hazards of transgene incorporation into host DNA are not warranted if short-term gene transfer is sufficient. Indeed, Hammond, et al. have discovered that a limited duration expression of an angiogenic protein is sufficient for substantial angiogenesis, and transient gene transfer for cardiovascular disease and peripheral disease processes is therapeutically adequate.

Human 293 cells, which are human embryonic kidney cells transformed with adenovirus E1A/E1B genes, typify useful permissive cell lines. However, other cell lines which allow replication-deficient adenoviral vectors to propagate therein can be used.

Construction of Recombinant Adenoviral Vectors

All adenoviral vectors used in the present invention can be constructed by the rescue recombination technique described in Graham, Virology, 163:614–617, 1988. Briefly, the transgene of interest is cloned into a shuttle vector that contains a promoter, polylinker and partial flanking adenoviral sequences from which E1A/E1B genes have been deleted. As the shuttle vector, plasmid pAC1 (Virology, 163:614–617, 1988) (or an analog) which encodes portions of the left end of the human adenovirus 5 genome (Virology, 163:614–617, 1988) minus the early protein encoding E1A and E1B sequences that are essential for viral replication, and plasmid ACCMVPLPA (J. Biol. Chem., 267:25129–25134, 1992) which contains polylinker, the CMV promoter and SV40 polyadenylation signal flanked by partial adenoviral sequences from which the E1A/E1B genes have been deleted can be exemplified. The use of plasmid pAC1 or ACCMVPLA facilitates the cloning process. The shuttle vector is then co-transfected with a plasmid which contains the entire human adenoviral 5 genome with a length too large to be encapsidated, into 293 cells. Co-transfection can be conducted by calcium phosphate precipitation or lipofection (Biotechniques, 15:868–872, 1993). Plasmid JM17 encodes the entire human adenovirus 5 genome plus portions of the vector pBR322 including the gene for ampicillin resistance (4.3 kb). Although JM17 encodes all of the adenoviral proteins necessary to make mature viral particles, it is too large to be encapsidated (40 kb versus 36 kb for wild type). In a small subset of co-transfected cells, rescue recombination between the transgene containing the shuttle vector such as plasmid pAC1 and the plasmid having the entire adenoviral 5 genome such as plasmid pJM17 provides a recombinant genome that is deficient in the E1A/E1B sequences, and that contains the transgene of interest but secondarily loses the additional sequence such as the pBR322 sequences during recombination, thereby being small enough to be encapsidated. With respect to the above method, successful results have been reported (Giordano, et al., Circulation, 88:I-139, 1993, and Giordano and Hammond, Clin. Res., 42:123A, 1994). The CMV driven β-galactosidase encoding adenovirus HCMVSP11acZ (Clin. Res., 42:123A, 1994) can be used to evaluate efficiency of gene transfer using X-gal treatment.

The initial mode of gene transfer uses adenoviral vectors as delineated above. The advantages of these vectors include the ability to effect high efficiency gene transfer (more than 60% of target organ cells transfected in vivo), the ease of obtaining high titer viral stocks and the ability of these vectors to effect gene transfer into cells such as cardiac myocytes which do not divide.

Tissue-Specific Promoters

The present invention also contemplates the use of cell targeting not only by delivery of the transgene into the coronary artery, or femoral artery, or other localized site for example, but also the use of tissue-specific promoters. By fusing, for example, tissue-specific transcriptional control sequences of left ventricular myosin light chain-2 ($MLC_{2v}$) or myosin heavy chain (MHC) to a transgene such as the VEGF-$A_{138}$ gene within the adenoviral construct, transgene expression is limited to ventricular cardiac myocytes. The efficacy of gene expression and degree of specificity provided by $MDC_{2v}$ and MHC promoters with lacZ have been determined, using the recombinant adenoviral system of the present invention. Cardiac-specific expression has been reported previously by Lee, et al.. (J. Biol. Chem., 267:15875–15885, 1992). The $MLC_{2v}$ promoter is comprised of 250 bp, and fits easily within the adenoviral-5 packaging constraints. The myosin heavy chain promoter, known to be a vigorous promoter of transcription, provides a reasonable alternative cardiac-specific promoter and is comprised of less than 300 bp. Other promoters, such as the troponin-C promoter, while highly efficacious and sufficiently small, does less than lack adequate tissue specificity. By using the $MLC_{2v}$ or MHC promoters and delivering the transgene in vivo, it is believed that the cardiac myocyte alone (that is without concomitant expression in endothelial cells, smooth muscle cells, and fibroblasts within the heart) will provide adequate expression of an angiogenic protein such as $VEGF-A_{138}$ to promote angiogenesis. Limiting expression to the cardiac myocyte also has advantages regarding the utility of gene transfer for the treatment of CHF. By limiting expression to the heart, one avoids the potentially harmful effect of angiogenesis in non-cardiac tissues such as the retina. In addition, of the cells in the heart, the myocyte would likely provide the longest transgene expression since the cells do not undergo rapid turnover; expression would not therefore be decreased by cell division and death as would occur with endothelial cells. Endothelial-specific promoters are already available for this purpose (Lee, et al., *J. Biol. Chem.,* 265:10446–10450, 1990).

In the present invention, with regard to the treatment of heart disease, targeting the heart by intracoronary injection with a high titer of the vector and transfecting all cell types is presently preferred.

Propagation and Purification of Adenovirus Vectors

Successful recombinant vectors can be plaque purified according to standard methods. The resulting viral vectors are propagated on 293 cells which provide E1A and E1B functions in trans, to titers in the preferred $10^{10}$–$10^{12}$ viral particles/ml range. Cells can be infected at 80% confluence and harvested 48 hours later. After 3 freeze-thaw cycles the cellular debris is pelleted by centrifugation and the virus purified by CsCl gradient ultracentrifugation (double CsCl gradient ultracentrifugation is preferred). Prior to in vivo injection, the viral stocks are desalted by gel filtration through Sepharose columns such as G25 Sephadex. The product is then filtered through a 0.3 micron filter, thereby reducing deleterious effects of intracoronary injection of unfiltered virus (life threatening cardiac arrhythmias) and promoting efficient gene transfer. The resulting viral stock has a final viral titer in the range of $10^{10}$–$10^{12}$ viral particles/ml. The recombinant adenovirus must be highly purified, with no wild-type (potentially replicative) virus. Impure constructs can cause an intense immune response in the host animal. From this point of view, propagation and purification may be conducted to exclude contaminants and wild-type virus by, for example, identifying successful recombinants with PCR using appropriate primers, conducting two rounds of plaque purification, and double CsCl gradient ultracentrifugation. The recombinant adenovirus can also be passed through an appropriately-sized filter prior to intracoronary injection Delivery of Recombinant Adenovirus Vectors The viral stock can be in the form of an injectable preparation containing pharmaceutically acceptable carrier such as saline, for example, as necessary. The final titer of the vector in the injectable preparation is preferably in the range of $10^7$–$10^{13}$ viral particles which allows for effective gene transfer. Other pharmaceutical carriers, formulations and dosages are described below. For delivery to the myocardium, the adenovirus transgene constructs are preferably delivered by direct intracoronary (or graft vessel) injection using standard percutaneous catheter based methods under fluoroscopic guidance, at an amount sufficient for the transgene to be expressed to a degree which allows for highly effective therapy. The injection should be made deeply into the lumen (about 1 cm within the arterial lumen) of the coronary arteries (or graft vessel), and preferably be made in both coronary arteries.

By injecting the material directly into the lumen of the coronary artery by coronary catheters, it is possible to target the gene rather effectively, and to minimize loss of the recombinant vectors to the proximal aorta during injection. The vector stock, preferably containing no wild-type virus, may be injected deeply into the lumen of one or both coronary arteries (or grafts), preferably into both the right and left coronary arteries (or grafts), and preferably in an amount of $10^{10}$–$10^{14}$ viral particles as determined by optical densitometry (more preferably $10^{11}$–$10^{13}$ viral particles, most preferably $10^{12}$ viral particles). This type of injection enables local transfection of a desired number of cells, especially cardiac myocytes, in the affected myocardium with angiogenic protein- or peptide-encoding genes, thereby maximizing therapeutic efficacy of gene transfer, and minimizing undesirable angiogenesis at extracardiac sites and the possibility of an inflammatory response to viral proteins. A ventricular myocyte-specific promoter may be used, for example, to securely enable expression limited to the cardiac myocytes so as to avoid the potentially harmful effects of angiogenesis in non-cardiac tissues such as the retina. Thus delivery of the transgenes in this matter may result in targeted gene expression in, for example, the cells of the left ventricle.

It has been found that gene expression when delivered in this manner does not occur in hepatocytes and viral RNA cannot be found in the urine at any time after intracoronary injection. Any variety of coronary catheter, or a Stack perfusion catheter, for example, can be used in the present invention. In addition, other techniques known to those having ordinary skill in the art can be used for transfer of genes to the arterial wall.

Clinical Applications

Stimulating angiogenesis in mammals by transfecting the cells with a polynucleotide coding for $VEGF-A_{138}$, $VEGF-A_{162}$, $VEGF-A_{182}$, or other 6b-modified VEGF protein may employ the procedure described by Giordano et al. in "Intracoronary Gene Transfer of Fibroblast Growth Factor-5 Increases Blood Flow and Contractile Function in an Ischemic Region of the Heart", Nature Medicine, Vol. 2 No. 5, pp. 534–539, May 1996 which is incorporated herein by reference. $VEGF-A_{138}$, $VEGF-A_{162}$, $VEGF-A_{182}$, or other 6b-modified VEGF protein should be released from cells infected by adenovirus vectors directing expression of $VEGF-A_{138}$, $VEGF-A_{162}$, $VEGF-A_{182}$, or other 6b-modified VEGF protein in cells of the heart. This releasability is also found in $VEGF-A_{121}$ and $VEGF-A_{165}$ but not in $VEGF-A_{189}$ or $VEGF-A_{206}$. However, $VEGF-A_{138}$, $VEGF-A_{162}$, $VEGF-A_{182}$, or other 6b-modified VEGF protein in contrast to $VEGF-A_{121}$, or $VEGF-A_{165}$, may be partially retained by ECM molecules as it diffuses towards target endothelial cells in adjacent blood vessels. The bound $VEGF-A_{138}$, $VEGF-A_{162}$, $VEGF-A_{182}$, or other 6b-modified VEGF protein may be slowly released later thus prolonging the angiogenic effect as compared to $VEGF-A_{121}$ or $VEGF-A_{165}$. Furthermore, the ECM bound $VEGF-A_{138}$, $VEGF-A_{162}$, $VEGF-A_{182}$, or other 6b-modified VEGF protein will be active, and will support the newly synthesized blood vessels during the critical period of blood vessel maturation, until the existence of blood vessels is no longer dependent upon the presence of angiogenic growth factors. Thus, $VEGF-A_{138}$, $VEGF-A_{162}$, $VEGF-A_{182}$, or other 6b-modified VEGF protein will be more effective than some other VEGF forms as a therapeutic agent to be used for induction of collateral blood vessels. These advantages may be critical when usage of adenovirus based expression vectors for gene therapy delivery of angiogenic agents is considered. An advantage of using adenovirus based vectors is that they are generally safe. Because the VEGF-$A_{138}$, VEGF-$A_{162}$, VEGF-$A_{182}$, or other 6b-modified VEGF protein may have binding characteristics that allow it to clear at a slower rate compared to some other secreted VEGF forms, they may be more effective therapeutic agents compared to the other VEGF forms.

Balloon angioplasty is a major treatment of ischemic heart disease which involves the inflation of a balloon in a clogged blood vessel in order to open the blocked blood vessel. Unfortunately, this method of treatment frequently results in injury to the endothelial cells lining the inner walls of blood vessels. Smooth muscle cells often infiltrate into the opened blood vessels causing a secondary obstruction in a process called restenosis. VEGF-$A_{138}$, VEGF-$A_{162}$, VEGF-$A_{182}$, or other 6b-modified VEGF protein may be employed to induce proliferation of the endothelial cells located at the periphery of the balloon induced damaged area in order to cover the luminal surface of the vessel with a new monolayer of endothelial cells, hoping to restore the original structure of the blood vessel. Adenovirus mediated gene therapy may also be applicable in this case as a method aimed at the delivery of inducers of endothelial cell proliferation to the lesion created by the balloon angioplasty procedure. The ability to bind to the ECM may offer several advantages for this application.

To prevent restenosis following balloon angioplasty, two types of approaches may be considered. It is possible to deliver a protein, or deliver an expression vector which will direct the expression of such a protein, to the site of occlusion using the balloon that is used to open the clogged vessel. Such a protein will also inhibit the proliferation of the non-endothelial cells which invade the reopened blood vessel until the endothelial cells on both sides of the wounded endothelial cells monolayer have a chance to re-grow. This can be combined with the delivery of a protein or a vector such as a recombinant adenovirus which will speed the re-growth of the endothelial cell layer. However, growth factors such as FGF-5, bFGF or HGF are also mitogenic to smooth muscle cells, and will induce their proliferation, which is the opposite of the desired effect. VEGFs on the other hand are generally specific for endothelial cells. VEGF-$A_{138}$, VEGF-$A_{162}$, VEGF-$A_{182}$, or other 6b-modified VEGF protein may be especially useful in this context, because of its ECM binding properties. Following application, for example, by infection of adjacent cells with adenovirus encoding the protein, direct transfection with plasmid DNA encoding the protein, or the direct delivery of the protein, VEGF-$A_{138}$, VEGF-$A_{162}$, VEGF-$A_{182}$, or other 6b-modified VEGF protein have the potential to stick to the exposed extracellular matrix in the balloon treated vessel, and thus promote proliferation and re-growth of endothelial cells specifically at the site of the lesion. Thus, VEGF-$A_{138}$, VEGF-$A_{162}$, VEGF-$A_{182}$, or other 6b-modified VEGF protein can localize and concentrate in the very region where its activity is required, making it a particularly attractive candidate for the treatment of restenosis.

Coronary angioplasty is frequently accompanied by deployment of an intravascular stent to help maintain vessel function and avoid restenosis. Stents have been coated with heparin to prevent thrombosis until the new channel formed by the stent can endothelialize. The 6b-modified VEGF protein can be applied directly to the stent, or nucleic acids encoding the 6b-modified protein, such as plasmids, cDNA, or adenovirus vectors, may be applied to the stent for direct transfection of neighboring cells, using methods known to those of skill in the art. VEGF-$A_{138}$, VEGF-$A_{162}$, VEGF-$A_{182}$, or other 6b-modified VEGF protein that is locally applied, or produced through transfection, will enhance endothelialization of the stent and thus reduce thrombosis and restenosis.

Other applications for use of the growth factor of the present invention are contemplated. One example is for the treatment of ulcers. An ulcer is in effect a wound residing in the stomach. It was shown that angiogenic growth factors may be effective for the treatment of duodenal ulcers, and that stabilization of angiogenic growth factors may be a mechanism by which some therapeutic agents such as sucralfate produce their beneficial effects (Szabo, S., et. al. *Gastroenterology* 106, 1106–1111, 1994). Since VEGF is an angiogenic growth factor that is very stable under acidic conditions, its employment for the treatment of stomach and duodenal ulcers is contemplated. The heparin binding ability of VEGF-$A_{138}$, VEGF-$A_{162}$, VEGF-$A_{182}$, or other 6b-modified VEGF protein which acts to preserve it in an active state, and its expected ability to bind to exposed ECM at the wound site, indicate that VEGF-$A_{138}$, VEGF-$A_{162}$, VEGF-$A_{182}$, or other 6b-modified VEGF protein may be more suitable than other VEGF forms for treating stomach and duodenal ulcers.

To assist in understanding the present invention, the following Examples are included that describe the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE I

Preparation of a Nucleic Acid Sequence Coding for VEGF-$A_{138}$

At least 5 differentially-spliced VEGF-A isoforms exist. These include VEGF-A 121, 145, 165, 189 and 206. (See FIG. 1, and Houck et. al. (1991) *Molecular Endocrinology* 5(12): 1806–1814 & Poltorack et. al. (1997) Journal of Biological Chemistry 272(11): 7151–7158). Only one of these, VEGF-$A_{206}$ (Houck et. al. (1991) *Molecular Endocrinology* 5(12): 1806–1814, includes an exon denoted as 6b. The proposed name, VEGF-$A_{138}$, reflects the composition of the processed isoform which would be 138 amino acids in length. Two strategies are employed for the construction of VEGF-$A_{138}$. In one strategy, VEGF-$A_{206}$ is cloned, and exon 6B is generated by polymerase chain reaction (PCR). In a second strategy, the replacement exon is generated by synthesis of two complementary oligonucleotides which are annealed to each other before sub-cloning. In both strategies, Exon 8 is excised in the first step and cloned back in at the last step. Exon 8 can be generated by PCR or by synthesis of complementary oligonucleotides. Synthesis of Exon 8 is described. Those of ordinary skill in the art will understand how to apply the teachings of the invention to the construction of VEGF-$A_{138}$, VEGF-$A_{162}$, VEGF-$A_{182}$ or other 6b-modified protein, using these or analogous strategies.

A. Background Information

1. Sequence of VEGF-$A_{145}$ (the sequence is shown with flanking BamHI sites; the insert is cloned into the Invitrogen vector, pCRII) [SEQ ID NO.1]. Exon 6a is shown in bold type. GGATCCGAAACCAT-GAACTTTCTGCTGTCTTGGGTGCATTG- GAGCCTTGCCTTGCTGCTCTACCTCCAC-
CATGCCAAGTGGTCCCAGGCTGCACCCATG
GCAGAAGGAGGAGGGCAGAATCATCAC-
GAAGTGGT
GAAGTTCATGGATGTCTATCAGCGCAGC-
TACTGCCATCCAATCGAGACCCTGGTG-
GACATCTTCCAGGAGTACCCTGAT-
GAGATCGAGTACATCTTCAAGCCATCCTGTG
TGCCCTGATGCGATGCGGGGCTGCTG-
CAATGACGAGGGCCTGGAGTGTGTGC-
CCACTGAGGAGTCCAACATCACCATGCA-
GATTATGCGGATCAAACCTCACCAAGGCC
AGCACATAGGAGAGATGAGCTTCCTA-
CAGCACAACAAATGTGAATGCAGAC-
CAAAGAAAGATAGAGCAAGACAA-
GAAAAAAAATCAGTTCGAGGAAAGGGAAAG
GGGCAAAAACGAAAGCGCAAGAAATC-
CCGGTATAAGTCCTGGAGCGTATGTGA-
CAAGCCGAGGCGGTGATGAATGAGGATCC 2. Sequence of the Replacement cassette (Exon 6b from VEGF-A$_{206}$) [SEQ ID NO.2]. GTACGTTGGTGC-CCGCTGCTGTCTAATGCCCTGGAGCCTC-CCTGGCCCCA B. Strategy for Subcloning VEGF-A$_{138}$ can be generated by replacement of the exon, 6a, of VEGF-A$_{145}$, with an alternative exon, 6b, which has been reported only in VEGF-A$_{206}$. The requisite steps are:

1. Generate a site-specific mutation in VEGF-A$_{145}$ that will allow restriction immediately 5' of Exon 6a (i.e., between nucleotides 434 and 435). This mutation will create Apo I site.

Nucleotides 437 and 438 will be converted, by site-directed mutagenesis from Adenines to Thymidine. This will change the existing sequence from "AAAAAT" to "AAATTT". (Apo I cleaves the site "Pu\AATTPy").

2. Excise Exon 6a and Exon 8 by restriction endonuclease cleavage of the site-specifically mutated VEGF-A$_{145}$ with Apo I and EcoR5. EcoR5 creates a blunt end in the vector, 3' of the VEGF insert.

3. Remove the Apo I 5' overhang by digestion with Mung Bean nuclease.

4. This will create a truncated, linearized, VEGF-A$_{145}$ vector. Gel-purify this vector.

5. Generate the replacement exon (see "A.2.", above) by PCR from VEGF-A$_{206}$ or by synthesis of complementary oligonucleotides.

a. For PCR, the 5' oligo would be:
    (n)$_6$tacGTACGTTGGTGCCCGCTGCT [SEQ ID NO.3]. The 3' oligo would be:
    ACCTCGGAGGGACCGGGGGccctatag(n)$_2$ [SEQ ID NO.4].

Uppercase letters represent nucleotides which comprise VEGF-A sequence.

Lowercase letters represent nucleotides added to create appropriate restriction sites for cloning.

The PCR product will be endonuclease restricted with SnaB1 (cleaves TAC/GTA) and EcoR5 (cleaves GAT/ATC).

Note that the 3' oligo does not include the most 5' nucleotide from Exon 6b. This nucleotide will be added to the Exon 8 thereby completing the requisite sequence and preserving the proper reading frame.

b. If the replacement exon is directly synthesized, the oligos will be:
    (n)$_6$tacGTACGTTGGTGCCCGCTGCTGTCTAATGC CCTGGAGCCTCCCTGGCCCCCgggatatc(n)$_2$ [SEQ ID NO:5] and its reverse complement.

After complementary oligonucleotides are annealed, they will be endonuclease restricted with SnaB1 (cleaves TAC/GTA) and EcoR5 (cleaves GAT/ATC).

6. After gel purification, ligate the replacement into the truncated, linearized VEGF-A$_{145}$. The product, pE-1–5/6b, contains Exons 1–5 and all but the most 3' nucleotide of Exon 6b.

7. Screen for proper orientation by restriction mapping.

8. Linearize pE1–5/6b. Endonuclease restriction with SmaI (cleaves at CCC/GGG) and NotI (cleaves at GC/GGCCGC). NotI will cleave 3' of the VEGF-A sequence in the pCRII-vector.

9. Generate Exon 8 by synthesis of the oligonucleoti de: AATGTGACAAGCCGAGGCGGTGATGAATGAAT GAGGATGCGGCCGCAAAAGGAA[SEQ ID NO. 6]

and its reverse complement. Those of ordinary skill in the art will recognize that this exon may also be synthesized using preferred codons of the cell type in which the transgene will be expressed.

10. After annealing, add 5' phosphates with T4 polynucleotide kinase.

11. Ligate the synthesized Exon 8 into the linearized vector p1–5/6b.

12. Screen for proper orientation by restriction mapping and confirm insert integrity by sequencing.

EXAMPLE II

Expression of VEGF-A$_{138}$

This recombinant VEGF-A$_{138}$ cDNA is used to construct fa recombinant baculovirus containing the VEGF-A$_{138}$ cDNA. The virus is used to infect Sf9 cells as described for VEGF-A$_{165}$ by Cohen, T., et al. *Growth Factors.* 7:131–138, 1992, incorporated herein by reference. Most of the VEGF-A$_{138}$ produced by the infected Sf9 cells should be found in the conditioned medium. Dithiotreitol may be used to dissociate VEGF-A$_{138}$ dimers for purification. VEGF-A$_{138}$ is partially purified using heparin-sepharose. The protein is eluted from the column using a stepwise salt gradient. The recombinant VEGF-A$_{138}$ is biologically active and induces the proliferation of human umbilical vein derived endothelial cells (HUVEC cells). Other 6b modified VEGF-A proteins can be expressed using analogous methods.

EXAMPLE III

Proliferation of Endothelial Cells and Angiogenesis

To confirm that VEGF-A$_{138}$ can induce angiogenesis in vivo, the VEGF-A$_{138}$ DNA is subcloned into the BamHI site of the mammalian expression vector MIRB using the technique described by Macarthur, C. A., et al. *Cell Growth Differ.* 6, 817–825, 1995, which is incorporated herein by reference. The MIRB/VEGF-A$_{138}$ plasmid is transfected into BHK-21 hamster kidney derived cells (a cell line that does not produce VEGF-A$_{145}$), and stable cell lines producing VEGF-A$_{138}$ are isolated. The VEGF-A$_{138}$ produced by the mammalian cells is biologically active and is secreted into the growth medium. The VEGF-A$_{138}$ expressing cells are embedded in alginate beads, and the beads are implanted under the skin of Balb/c mice using the method described by Plunkett, M. L., et. al. *Lab. Invest.* 62, 510–517, 1990, which is incorporated herein by reference. Alginate pellets containing the entrapped cells are removed after four days and photographed. Clusters of alginate beads containing VEGF-A$_{138}$ expressing cells are dark red with blood, while beads containing cells transfected with vector alone have a much lower content of blood. When examined under higher magnification, pellets containing VEGF-A$_{138}$ producing cells appear much more vascularized than pellets containing control cells. These results are consistent with the expected behavior of a vascular cell proliferation or angiogenesis-promoting factor.

EXAMPLE IV
Gene-Transfer-Mediated Angiogenesis Therapy Using VEGF-A$_{138}$ DNA encoding VEGF-A$_{138}$, VEGF-A$_{162}$, VEGF-A$_{182}$, or other 6b-modified VEGF protein is used for gene-transfer-mediated angiogenesis therapy as described, for example, in International Patent Application No. PCT/US96/02631, published Sep. 6, 1996, as WO 96/26742, hereby incorporated by, reference herein in its entirety.

Adenoviral Constructs

A helper independent replication deficient human adenovirus 5 system may be used for gene-transfer. A nucleic acid molecule coding for VEGF-A$_{138}$, VEGF-A$_{162}$, VEGF-A$_{182}$, or other 6b-modified VEGF protein may be cloned into the polylinker of plasmid ACCMVPLPA which contains the CMV promoter and SV40 polyadenylation signal flanked by partial adenoviral sequences from which the E1A and E1B genes (essential for viral replication) have been deleted. This plasmid is co-transferred (lipofection) into 293 cells with plasmid JM17 which contains the entire human adenoviral 5 genome with an additional 4.3 kb insert making pJM17 too large to be encapsulated. Homologous rescue recombination results in adenoviral vectors containing the transgene in the absence of E1A/E1B sequences. Although these recombinants are nonreplicative in mammalian cells, they can propagate in 293 cells which have been transformed with E1A/E1B and provided these essential gene products in trans. Transfected cells are monitored for evidence of cytopathic effect which usually occurs 10–14 days after transfection. To identify successful recombinants, cell supernatant from plates showing a cytopathic effect is treated with proteinase K (50 mg/ml with 0.5% sodium dodecyl sulfate and 20 mM EDTA) at 56° C. for 60 minutes, phenol/chloroform extracted and ethanol precipitated. Successful recombinants are then identified with PCR using primers (*Biotechniques*, 15:868–72, 1993) complementary to the CMV promoter and SV40 polyadenylation sequences to amplify the VEGF-A$_{138}$, VEGF-A$_{162}$, VEGF-A$_{182}$, or other 6b-modified VEGF protein nucleic acid insert and primers (*Biotechniques*, 15:868–72, 1993) designed to concomitantly amplify adenoviral sequences. Successful recombinants then are plaque purified twice. Viral stocks are propagated in 293 cells to titers ranging between $10^{10}$ and $10^{12}$ viral particles, and are purified by double CsCl gradient centrifugation prior to use. The system used to generate recombinant adenoviruses imposed a packing limit of 5 kb for transgene inserts. The VEGF-A$_{138}$, VEGF-A$_{162}$, VEGF-A$_{182}$, or other 6b-modified VEGF protein genes, driven by the CMV promoter and with the SV40 polyadenylation sequences are well within the packaging constraints. Recombinant vectors are plaque purified by standard procedures. The resulting viral vectors are propagated on 293 cells to titers in the $10^{10}$–$10^{12}$ viral particles range. Cells are infected at 80% confluence and harvested at 36–48 hours. After freeze-thaw cycles the cellular debris is pelleted by standard centrifugation and the virus further purified by double CsCl gradient ultracentrifugation (discontinuous 1.33/1.45 CsCl gradient: cesium prepared in 5 mM Tris, 1 mM EDTA (pH 7.8); 90,000×g (2 hr), 105,000×g (18 hr)). Prior to in vivo injection, the viral stocks are desalted by gel filtration through Sepharose columns such as G25 Sephadex. The resulting viral stock has a final viral titer approximately in the $10^{10}$–$10^{12}$ viral particles range. The adenoviral construct should thus be highly purified, with no wild-type (potentially replicative) virus.

Porcine Ischemia Model for Angiogenesis

A left thoracotomy is performed on domestic pigs (30–40 kg) under sterile conditions for instrumentation. (Hammond, et al., *J. Clin Invest* 92:2644–52, and Roth, et al., *J. Clin. Invest.* 91:939–49, 1993). Catheters are placed in the left atrium and aorta, providing a means to measure regional blood flow, and to monitor pressures. Wires are sutured on the left atrium to permit ECG recording and atrial pacing. Finally, an ameroid is placed around the proximal LCx. After a stable degree of ischemia develops, the treatment group receives an adenoviral construct that includes a VEGF-A$_{138}$, VEGF-A$_{162}$, VEGF-A$_{182}$, or other 6b-modified VEGF protein gene driven by a CMV promoter. Control animals receive gene transfer with an adenoviral construct that includes a reporter gene, lacZ, driven by a CMV promoter.

Studies are initiated 35±3 days after ameroid placement, at a time when collateral vessel development and pacing-induced dysfunction are stable (Roth, et al., *Am. J. Physiol* 253: 1-11279–1288, 1987, and Roth, et al., *Circulation* 82:1778–89). Conscious animals are suspended in a sling and pressures from the LV, LA and aorta, and electrocardiogram are recorded in digital format on-line (at rest and during atrial pacing at 200 bpm). Two-dimensional and M-mode images are obtained using a Hewlett Packard ultrasound imaging system. Images are obtained from a right parastemal approach at the mid-papillary muscle level and recorded on VHS tape. Images are recorded with animals in a basal state and again during right atrial pacing (HR=200 bpm). These studies are performed one day prior to gene transfer and repeated 14±1 days later. Rate-pressure products and left atrial pressures should be similar in both groups before and after gene transfer, indicating similar myocardial oxygen demands and loading conditions. Echocardiographic measurements are made using standardized criteria (Sahn, et al., *Circulation* 58:1072, 1978). End-diastolic wall thickness (EDWTh) and end-systolic wall thickness (ESWTh) are measured from 5 continuous beats and averaged. Percent wall thickening (% WTh) is calculated [(EDWTh-ESWTh)/ EDWTh]×100. Data should be analyzed without knowledge of which gene the animals had received. To demonstrate reproducibility of echocardiographic measurements, animals should be imaged on two consecutive days, showing high correlation ($r^2$=0.90; p=0.005).

35±3 days after ameroid placement, well after ameroid closure, but before gene transfer, contrast echocardiographic studies are performed using the contrast material (Levovist) which is injected into the left atrium during atrial pacing (200 bpm). Studies are repeated 14±1 days after gene transfer. Peak contrast intensity is measured from the video images using a computer-based video analysis program (Color Vue II, Nova Microsonics, Indianapolis, Ind.), that provides an objective measure of video intensity. The contrast studies are analyzed without knowledge of which gene the animals have received.

At completion of the study, animals are anesthetized and midline thoracotomy performed. The brachycephalic artery is isolated, a canula inserted, and other great vessels ligated. The animals receive intravenous heparin (10,000 IU) and papaverine (60 mg). Potassium chloride is given to induce diastolic cardiac arrest, and the aorta cross-clamped. Saline is delivered through the brachycephalic artery cannula (120 mm Hg pressure), thereby perfusing the coronary arteries. Glutaraldehyde solution (6.25%, 0.1 M cacodylate buffer) was perfused (120 mm Hg pressure) until the heart is well fixed (10–15 min). The heart is then removed, the beds identified using color-coded dyes injected anterograde through the left anterior descending (LAD), left circumflex (LCx), and right coronary arteries. The ameroid is examined to confirm closure. Samples taken from the normally perfused and ischemic regions are divided into thirds and the endocardial and epicardial thirds are plastic-imbedded. Microscopic analysis to quantitate capillary number is conducted as previously described (Mathieu-Costello, et al., Am. J. Physiol 359:H204, 1990). Four 1 μm thick transverse sections are taken from each subsample (endocardium and epicardium of each region) and point-counting is used to determine capillary number per fiber number ratio at 400× magnification. Twenty to twenty-five high power fields are counted per subsample. Within each region, capillary number to fiber number rations should be similar in endocardium and epicardium so the 40–50 field per region should be averaged to provide the transmural capillary to fiber number ratio.

To establish that improved regional function and blood flow result from transgene expression, PCR and RT-PCR may be used to detect transgenic VEGF-$A_{138}$, VEGF-$A_{162}$, VEGF-$A_{182}$, or other 6b-modified VEGF protein DNA and mRNA in myocardium from animals that have received VEGF$_{38}$, VEGF-$A_{162}$, VEGF-$A_{182}$, or other 6b-modified VEGF protein gene transfer. Using a sense primer to the CMV promoter [GCAGAGCTCGTTTAGTGAAC] and antisense [SEQ ID NO. 7] primer to the internal VEGF-$A_{138}$, VEGF-$A_{162}$, VEGF-$A_{182}$, or other 6b-modified VEGF protein gene sequence PCR is used to amplify the expected 500 bp fragment. Using a sense primer to the beginning of the VEGF-$A_{138}$, VEGF-$A_{162}$, VEGF-$A_{182}$, or other 6b-modified VEGF protein sequence and an antisense primer to the internal VEGF-$A_{138}$, VEGF-$A_{162}$, VEGF-$A_{182}$, or other 6b-modified VEGF protein gene sequence RT-PCR is used to amplify the expected 400 bp fragment.

Finally, using an antibody directed against VEGF$_{145}$ VEGF-$A_{138}$, VEGF-$A_{162}$, VEGF-$A_{182}$, or other 6b-modified VEGF protein, protein expression maybe demonstrated 48 hours as well as 14±1 days after gene transfer in cells and myocardium from animals that have received gene transfer with a VEGF-$A_{138}$, VEGF-$A_{162}$, VEGF-$A_{182}$, or other 6b-modified VEGF protein gene.

The helper independent replication deficient human adenovirus 5 system can be employed to prepare transgene containing vectors. The material injected in vivo should be highly purified and should preferably contain no wild-type (replication competent) adenovirus. Thus adenoviral infection and inflammatory infiltration in the heart are minimized. By injecting the material directly into the lumen of the coronary artery by coronary catheters, it is possible to target the gene effectively. When delivered in this manner there should be no transgene expression in hepatocytes, and viral RNA should not be found in the urine at any time after intracoronary injection.

Injection of the construct (4.0 ml containing about $10^{11}$ viral particles of adenovirus) can be performed by injecting 2.0 ml into both the left and right coronary arteries (collateral flow to the LCx bed appeared to come from both vessels). Animals are anesthetized, and arterial access acquired via the right carotid by cut-down; a 5F Cordis sheath is then placed. A 5F Multipurpose (A2) coronary catheter is used to engage the coronary arteries. Closure of the LCx ameroid is confirmed by contrast injection into the left main coronary artery. The catheter tip is then placed 1 cm within the arterial lumen so that minimal material is lost to the proximal aorta during injection. This procedure is carried out for each of the pigs.

Once gene transfer is performed, three strategies are used to establish successful incorporation and expression of the gene: (1) Some constructs may include a reporter gene (lacZ); (2) myocardium from the relevant beds is sampled, and immunoblotting is performed to quantitate the presence of VEGF$_{145}$ protein; and (3) PCR is used to detect VEGF-$A_{138}$, VEGF-$A_{162}$, VEGF-$A_{182}$, or other 6b-modified VEGF protein mRNA and DNA.

The regional contractile function data obtained should show that control pigs show a similar degree of pacing-induced dysfunction in the ischemic region before and 14±1 days after gene transfer. In contrast, pigs receiving VEGF-$A_{138}$, VEGF-$A_{162}$, VEGF-$A_{182}$, or other 6b-modified VEGF protein gene transfer should show an increase in wall thickening in the ischemic region during pacing, demonstrating that VEGF-$A_{138}$, VEGF-$A_{162}$, VEGF-$A_{182}$, or other 6b-modified VEGF protein gene transfer in accordance with the invention is associated with improved contraction in the ischemic region during pacing. Wall thickening in the normally perfused region (the interventricular septum) should be normal during pacing and unaffected by gene transfer. The percent decrease in function measured by transthoracic echocardiography should be very similar to the percentage decrease measured by sonomicrometry during atrial pacing in the same model (Hammond, et al. J. Clin. Invest. 92:2644, 1993), documenting the accuracy of echocardiography for the evaluation of ischemic dysfunction.

Although preferred embodiments are specifically described herein, it will be appreciated that many modifications and variations of the present invention are possible in light of the above teachings and within the purview of the appended claims without departing from the spirit and intended scope of the invention.

We claim:

1. A nucleic acid sequence, encoding a 6b- modified human VEGF-A polypeptide, comprising exons 1–5, 6b and 8 of VEGF-A and lacking exon 7 of VEGF-A.

2. The nucleic acid sequence of claim 1, encoding the amino acid sequence of SEQ ID NO 24.

3. The nucleic acid sequence of claim 1, encoding the amino acid sequence of SEQ ID NO 28.

4. An expression vector comprising a nucleic acid according to claim 1.

5. The expression vector according to claim 4, wherein said nucleic acid encodes the amino acid sequence of SEQ ID NO 24.

6. The expression vector according to claim 4, wherein said nucleic acid encodes the amino acid sequence of SEQ ID NO 28.

* * * * *